US009764122B2

(12) United States Patent
Clay et al.

(10) Patent No.: US 9,764,122 B2
(45) Date of Patent: Sep. 19, 2017

(54) DRUG DELIVERY DEVICE AND METHODS HAVING AN OCCLUDING MEMBER

(71) Applicant: Warsaw Orthopedic, Inc., Warsaw, IN (US)

(72) Inventors: Danielle L. Clay, Pleasant Prairie, WI (US); Lloyd Snyder, Collierville, TN (US); Jeffrey A. Soucia, Germantown, TN (US); Michael Merves, Collierville, TN (US); Antonio Belton, Richton Park, IL (US); Sean Corrigan, Chicago, IL (US); Keith Grider, Chicago, IL (US); Michael Honsing Lau, Chicago, IL (US); Derek Leatzow, Chicago, IL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 348 days.

(21) Appl. No.: 14/341,256

(22) Filed: Jul. 25, 2014

(65) Prior Publication Data
US 2016/0022974 A1 Jan. 28, 2016

(51) Int. Cl.
*A61M 31/00* (2006.01)
*A61M 37/00* (2006.01)
*A61M 5/315* (2006.01)

(52) U.S. Cl.
CPC .... *A61M 37/0069* (2013.01); *A61M 5/31511* (2013.01); *A61M 5/31576* (2013.01); *A61M 2205/32* (2013.01); *A61M 2205/584* (2013.01); *A61M 2205/60* (2013.01)

(58) Field of Classification Search
CPC ........ A61M 2205/32; A61M 2205/584; A61M 2205/60; A61M 37/0069; A61M 5/31511; A61M 5/31576
See application file for complete search history.

(56) References Cited

U.S. PATENT DOCUMENTS

| 4,105,030 | A | 8/1978 | Kercso |
| 4,451,253 | A | 5/1984 | Harman |
| 5,024,655 | A | 6/1991 | Freeman et al. |
| 5,207,678 | A | 5/1993 | Harms et al. |
| 5,212,162 | A | 5/1993 | Missel et al. |
| 5,756,127 | A | 5/1998 | Grisoni et al. |
| 6,203,813 | B1 | 3/2001 | Gooberman |
| 6,471,688 | B1 | 10/2002 | Harper et al. |
| 6,478,776 | B1 | 11/2002 | Rosenman et al. |
| 6,530,934 | B1 | 3/2003 | Jacobsen et al. |

(Continued)

*Primary Examiner* — Rebecca E Eisenberg

(57) ABSTRACT

Drug depot delivery devices and methods for delivering a drug depot to a site beneath the skin of a patient are provided. In various embodiments the device has a housing having a top housing end, and a bottom housing end. The housing defines a housing channel. The device has a drug cartridge defining a depot channel aligned with the housing channel and configured to slidably accept the drug depot. The drug cartridge has at least a first occluding device configured to occlude the depot channel at a first position such that the drug depot cannot pass through the depot channel without force applied to the drug depot sufficient to deflect the first occluding device. The bottom end of the housing has a coupling configuration for engaging a cannula. A plunger has a push rod to expel the drug depot through the occluding device and the cannula.

20 Claims, 12 Drawing Sheets

(56) References Cited

U.S. PATENT DOCUMENTS

| | | |
|---|---|---|
| 6,735,475 B1 | 5/2004 | Whitehurst et al. |
| 6,971,998 B2 | 12/2005 | Rosenman et al. |
| 7,001,892 B1 | 2/2006 | Chmielewski et al. |
| 7,252,651 B2 | 8/2007 | Haider et al. |
| 2001/0031940 A1* | 10/2001 | Loos ................. A61M 37/0069 604/15 |
| 2001/0043915 A1 | 11/2001 | Frey |
| 2004/0015133 A1 | 1/2004 | Karim |
| 2004/0064193 A1 | 4/2004 | Evans et al. |
| 2004/0111118 A1 | 6/2004 | Hill et al. |
| 2004/0220545 A1 | 11/2004 | Heruth et al. |
| 2004/0220546 A1 | 11/2004 | Heruth et al. |
| 2004/0220547 A1 | 11/2004 | Heruth et al. |
| 2004/0220548 A1 | 11/2004 | Heruth et al. |
| 2005/0070843 A1 | 3/2005 | Gonzales |
| 2005/0074481 A1 | 4/2005 | Brekke et al. |
| 2005/0137579 A1 | 6/2005 | Heruth et al. |
| 2005/0152949 A1 | 7/2005 | Hotchkiss et al. |
| 2005/0177118 A1 | 8/2005 | Hoganson et al. |
| 2005/0245906 A1 | 11/2005 | Makower et al. |
| 2005/0249775 A1 | 11/2005 | Falolico et al. |
| 2006/0046961 A1 | 3/2006 | McKay et al. |
| 2006/0253100 A1 | 11/2006 | Burright et al. |
| 2006/0264839 A1 | 11/2006 | Veasey et al. |
| 2007/0055378 A1 | 3/2007 | Ankney et al. |
| 2007/0219564 A1 | 9/2007 | Rue et al. |
| 2008/0228193 A1 | 9/2008 | Matityahu |
| 2012/0053561 A1* | 3/2012 | Simonton ......... A61M 37/0069 604/506 |

\* cited by examiner

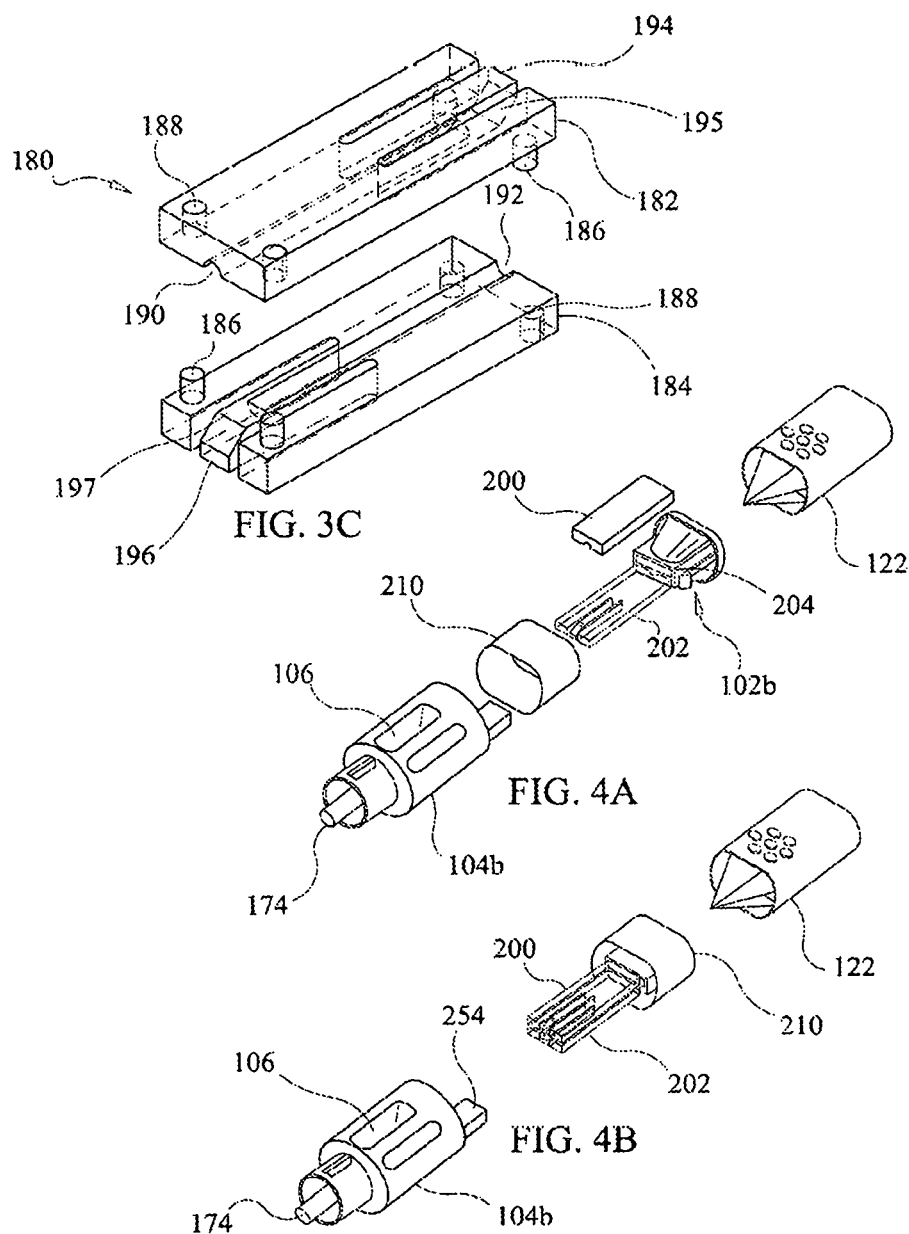

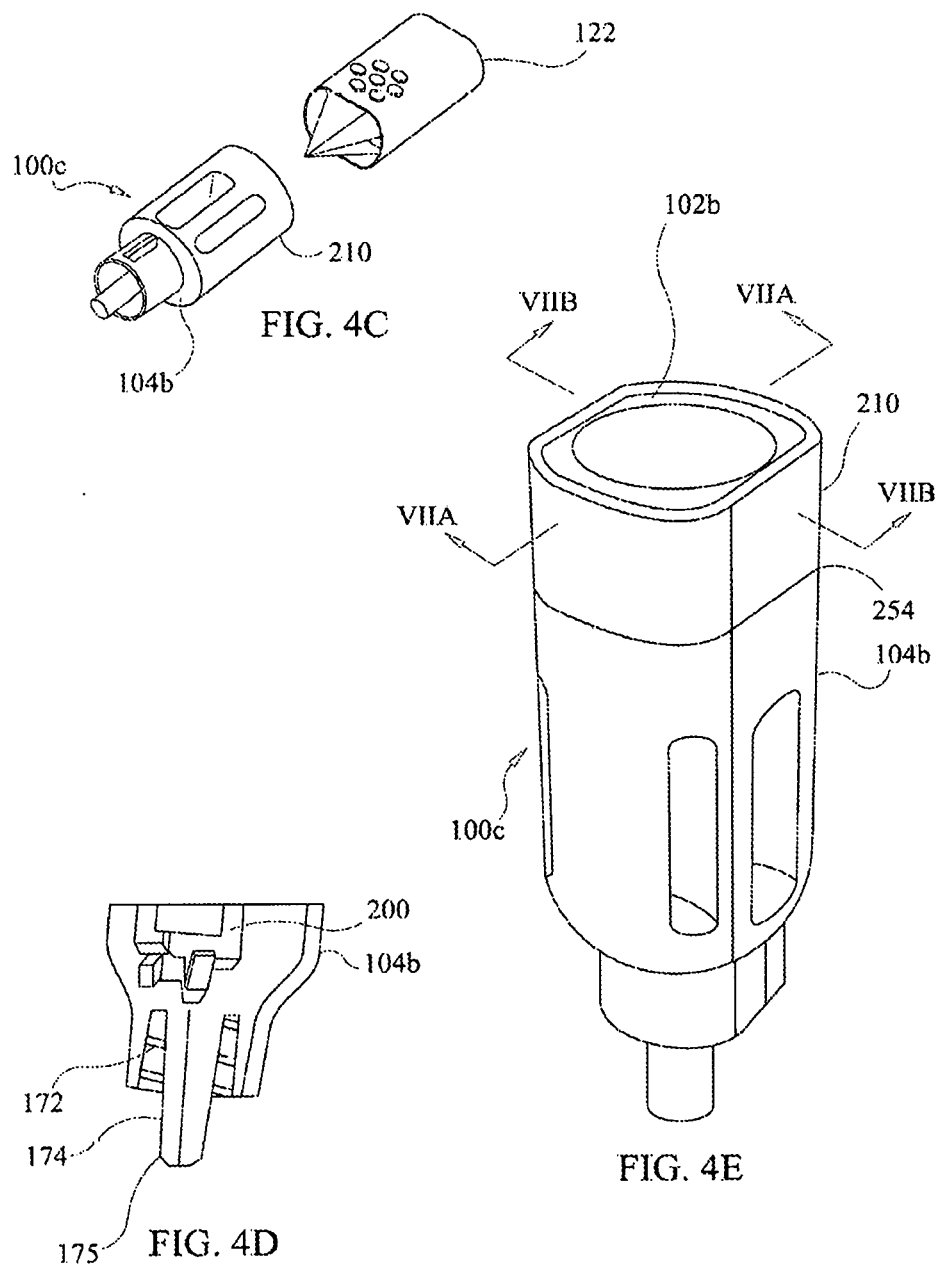

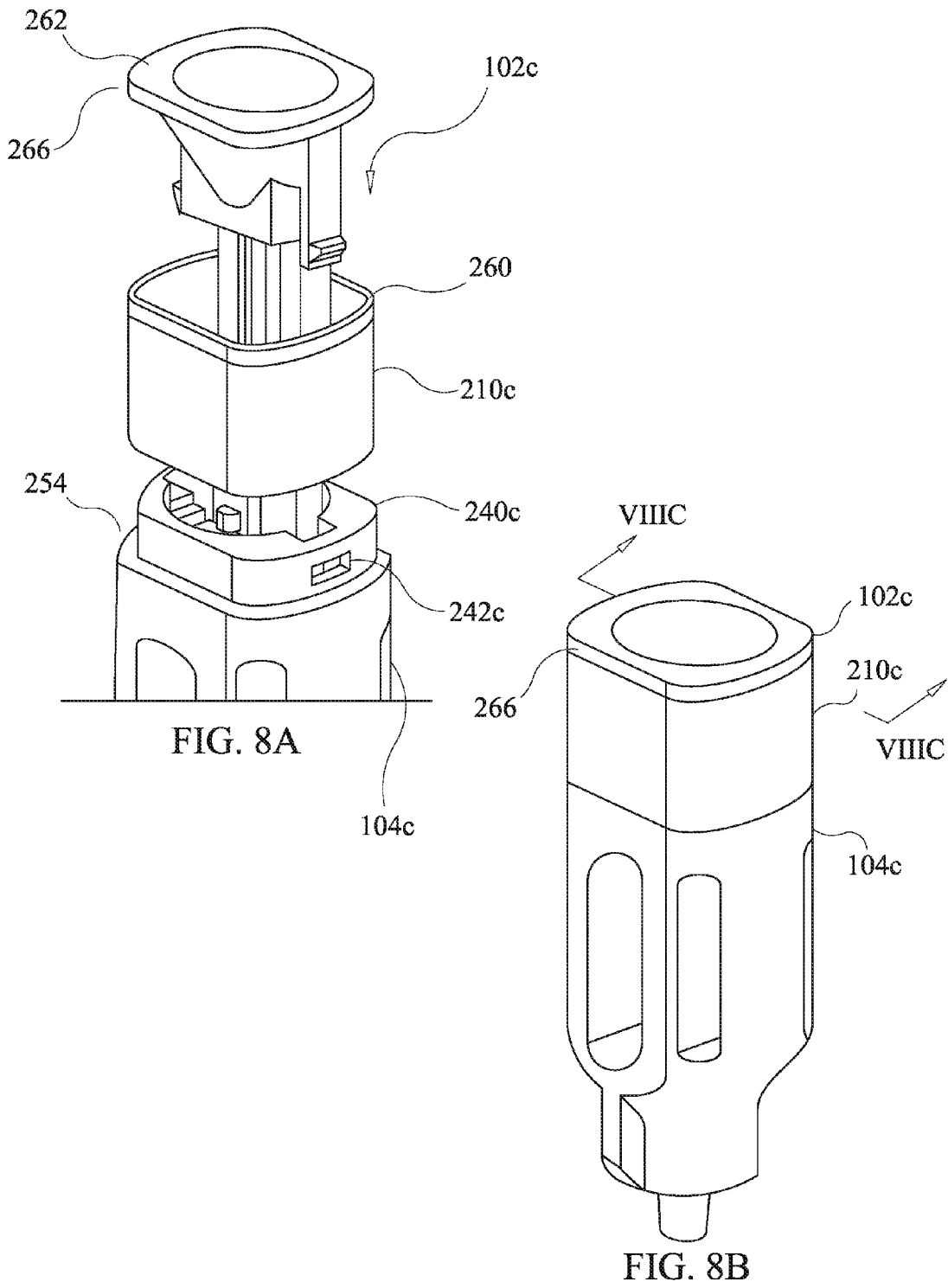

DRUG DELIVERY DEVICE AND METHODS HAVING AN OCCLUDING MEMBER

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient so that the drug is slowly released over a long period of time. Such drug depots allow the drug to be released from the depot in a relatively uniform dose over weeks, months or even years. This method of administering drugs is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Previously, drug depots and other types of implants have been inserted into the treatment site beneath the skin by use of a trocar device, which is a two-piece device that includes a cannula and an obdurator. The trocar device requires an incision to be made through the skin at the site of implant of the drug depot using a separate instrument (e.g., scalpel). A cannula and obdurator are inserted together through the skin at the incision site. Next, the obdurator is withdrawn, leaving the cannula in place as a guide for inserting the drug depot. The drug depot is inserted through the cannula, and the obdurator is used to push the implant to the end of the cannula. The cannula and obdurator are then withdrawn completely, leaving the implant in place beneath the skin.

Typically, trocar devices are used to implant drug depots subcutaneously over a large area (e.g., 2-2.5 inches), with a typical drug depot in the order of 1½ inches long. Thus, the trocar device is not suitable for many treatment sites because it lacks precision and may cause additional trauma to the tissue surrounding the site of implant.

Other drug delivery devices have been developed to simplify implanting the drug depots. These devices have a handle for one-handed implantation of the drug depot, a needle containing the drug depot to be implanted and a rod positioned within the needle for pushing the drug depot out of the needle. Once the needle containing the drug depot has been inserted at the site of implant, a spring loaded trigger on the handle is activated which causes the needle to be automatically withdrawn by a spring leaving the implanted drug depot in place. Unfortunately, it is not possible to control the motion of the needle in these devices because the needle will automatically retract upon activation of the trigger. The complex spring loaded propelling system and trigger of these devices increase the chances that the device will jam and fail to eject the drug depot when required.

Conventional needle and syringe devices have been used to implant a drug depot to sites such as, for example, the epidural space. These devices typically utilize a syringe preloaded with the drug depot and an epidural needle. The needle is inserted through the skin, supraspinus ligament, intraspinus ligament, ligamentum flavum and then into the epidural space. The drug depot is delivered through the needle to the epidural space using the syringe plunger. Conventional needle and syringe devices often do not easily allow controlled and precision implant of the drug depot. If multiple drug depot implants are needed, these conventional needle and syringe devices often do not allow accurate placement of the implant in a manner so that one drug depot does not substantially interfere with the dissolution of the other.

In certain methods of drug depot implantation, the drug depots are secured in the drug cartridge by use of a bulking agent. The bulking agent may be added to the drug depot to ensure the drug depot is secure within the chamber, such that the drug depot is released when a plunger is engaged to dislodge the drug depot from the cartridge. The bulking agent is sometimes added to the drug chamber before the drug depot is added to the chamber. Other times the drug depot is added to the drug chamber first and then the drug depot is added to the chamber. Use of a bulking agent to retain the drug depot in a drug cartridge requires additional steps and is time consuming. Thus, a drug delivery device which reduces a need for use of bulking agents is needed.

New drug delivery devices are needed, which can easily allow accurate and precise implantation of a drug depot with minimal physical and psychological trauma to a patient. When implanting several drug depots, a drug delivery device is needed that accurately and precisely allows placement of the drug depot in a manner such that one depot does not substantially interfere with the dissolution of the others.

SUMMARY

New drug delivery devices, which can easily allow accurate and precise implantation of a drug depot with minimal physical and psychological trauma to a patient are provided.

Briefly stated, provided are embodiments of drug delivery devices and methods for delivering a drug depot to a site beneath the skin of a patient. In various embodiments the device has a housing having a top housing end, and a bottom housing end. The housing defines a housing channel. The device has a drug cartridge defining a depot channel aligned with the housing channel and configured to slidably accept the drug depot. The drug cartridge has at least a first occluding device configured to occlude the depot channel at a first position such that the drug depot cannot pass through said depot channel without force applied to the drug depot sufficient to deflect the first occluding device. The bottom end of the housing has a coupling configuration for engaging a cannula. A plunger has a push rod to expel the drug depot through the occluding device and the cannula.

The present disclosure provides a drug delivery device, in various embodiments, for delivering a drug depot to a site beneath the skin of patient via a cannula having a proximal end and a distal end, the proximal end of the cannula having an opening to receive the drug depot, the distal end of the cannula being configured for insertion to the site beneath the skin of the patient and having an opening for passage of the drug depot.

The device comprises a housing having a top housing end, and a bottom housing end. The housing defines a housing channel having a housing channel first open end open to the top housing end and a second housing channel open end open to the bottom housing end. A drug cartridge defines a depot channel aligned with the housing channel and configured to slidably accept the drug depot. The drug cartridge has at least a first occluding device configured to occlude the depot channel at a first occluding position such that the drug depot cannot pass through the depot channel at the first occluding position without force, greater than that of gravity, applied to the drug depot sufficient to deflect the first occluding device an amount permitting passage of the drug depot past the first occluding device. The bottom end of the housing has a coupling configuration for engaging the proximal end of the cannula. A plunger has a push rod slidably receivable in the housing channel and the cannula and having a push rod end to contact the drug depot when disposed in the drug cartridge and, upon application of force, expel the drug depot through the first occluding device and the cannula to the site beneath the skin of the patient.

In one embodiment of the present disclosure, there is provided a kit for delivering a drug depot to a site beneath the skin of a patient, the kit comprising: a sterilized drug delivery device to be used in conjunction with a cannula having a proximal end and a distal end, the proximal end of the cannula having an opening to receive the drug depot, the distal end of the cannula being configured for insertion to the site beneath the skin of the patient and having an opening for passage of the drug depot. The kit comprises a housing having a top housing end, and a bottom housing end, the housing further defining a housing channel having a housing channel first open end open to the top end and a second housing channel open end open to the bottom end. Also provided is a drug cartridge defining a depot channel disposed to be aligned with the housing channel and configured to slidably accept the drug depot, the drug cartridge having at least a first occluding device configured to occlude the depot channel at a first occluding position such that the drug depot cannot pass through the depot channel at the first occluding position without force, greater than that of gravity, applied to the drug depot sufficient to deflect the first occluding device an amount permitting passage of the drug depot past the first occluding device. The bottom end of the housing has a coupling configuration for engaging the proximal end of the cannula. A plunger is provided having a push rod slidably receivable in the housing channel and the cannula and having a push rod end to contact the drug depot when disposed in the drug cartridge and, upon application of force, expel the drug depot through either of the first occluding device and the cannula to the site beneath the skin of the patient.

In another embodiment, a method of delivering a drug depot to a target site beneath the skin is provided. The method comprises inserting a cannula at the target tissue site, the cannula having a proximal end and a distal end, the proximal end of the cannula having an opening to receive a drug pellet, the distal end of the cannula configured for insertion to the target site beneath the skin of the patient and having an opening for passage of the drug pellet; and loading a drug delivery device with at least one drug depot. The drug delivery device comprises a housing having a top housing end, and a bottom housing end. The housing defines a housing channel having a housing channel first open end open to the top end and a second housing channel open end open to the bottom end. A drug cartridge defines a depot channel aligned with the housing channel and configured to slidably accept the drug depot. The drug cartridge has at least a first occluding device configured to occlude the depot channel at a first occluding position such that the drug depot cannot pass through the depot channel at the first occluding position without force, greater than that of gravity, applied to the drug depot sufficient to deflect the first occluding device an amount permitting passage of the drug depot past the first occluding device. The bottom end of the housing has a coupling configuration for engaging the proximal end of the cannula. A plunger has a push rod slidably receivable in the housing channel and the cannula and having a push rod end to contact the drug depot when disposed in the drug cartridge and, upon application of force, expel the drug depot through the first occluding device and the cannula to the site beneath the skin of the patient. The method further includes attaching the drug delivery device to the proximal end of the cannula, and inserting the push rod of the plunger into the housing channel of the drug delivery device and applying force to expel the drug depot through the first occluding device and the cannula to the site beneath the skin of the patient.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 1a is a front elevation view of a first embodiment of a drug delivery device of the present disclosure;

FIG. 1b is front, left side and top perspective view of the first embodiment of FIG. 1a;

FIG. 1c is a front elevation view of a plunger of the embodiment of FIG. 1a;

FIG. 1d is a front elevation view of a housing of the embodiment of FIG. 1a;

FIG. 1e is a left side elevation view of a housing of the embodiment of FIG. 1a;

FIG. 3c is an exploded perspective view of a drug cartridge of the embodiment of FIG. 3a;

FIG. 4a is an exploded front, right side, and bottom perspective view of a third embodiment of a drug delivery device of the present disclosure;

FIG. 4b is an exploded front, right side, and bottom perspective view of the third embodiment of a drug delivery device of the present disclosure showing embodiments of a drug cartridge, funnel body, and ring member in an assembled state;

FIG. 4c is an exploded front, right side, and bottom perspective view of the third embodiment of a drug delivery device of the present disclosure showing the assembly of the embodiment of a drug cartridge, funnel body, and ring member assembled together with an embodiment of a housing body of the third embodiment;

FIG. 4d is a cross-sectional view of a portion of the housing of FIG. 4c with the drug cartridge of FIG. 4c installed;

FIG. 4e is a front, right side, and top perspective view of an assembled housing of the third embodiment of a drug delivery device of the present disclosure;

FIG. 5b is a cross-sectional view of the funnel body of FIG. 5a;

FIG. 6b is a front side, left side, and top perspective view of the housing body of FIG. 6a;

FIG. 8a is an exploded partial front, right side, and top side perspective view of the housing of a fourth embodiment of a drug delivery device of the present disclosure;

FIG. 8b is a front side, right side, and top side perspective view of the housing of FIG. 8a in an assembled state;

Figures 1A, 1B:
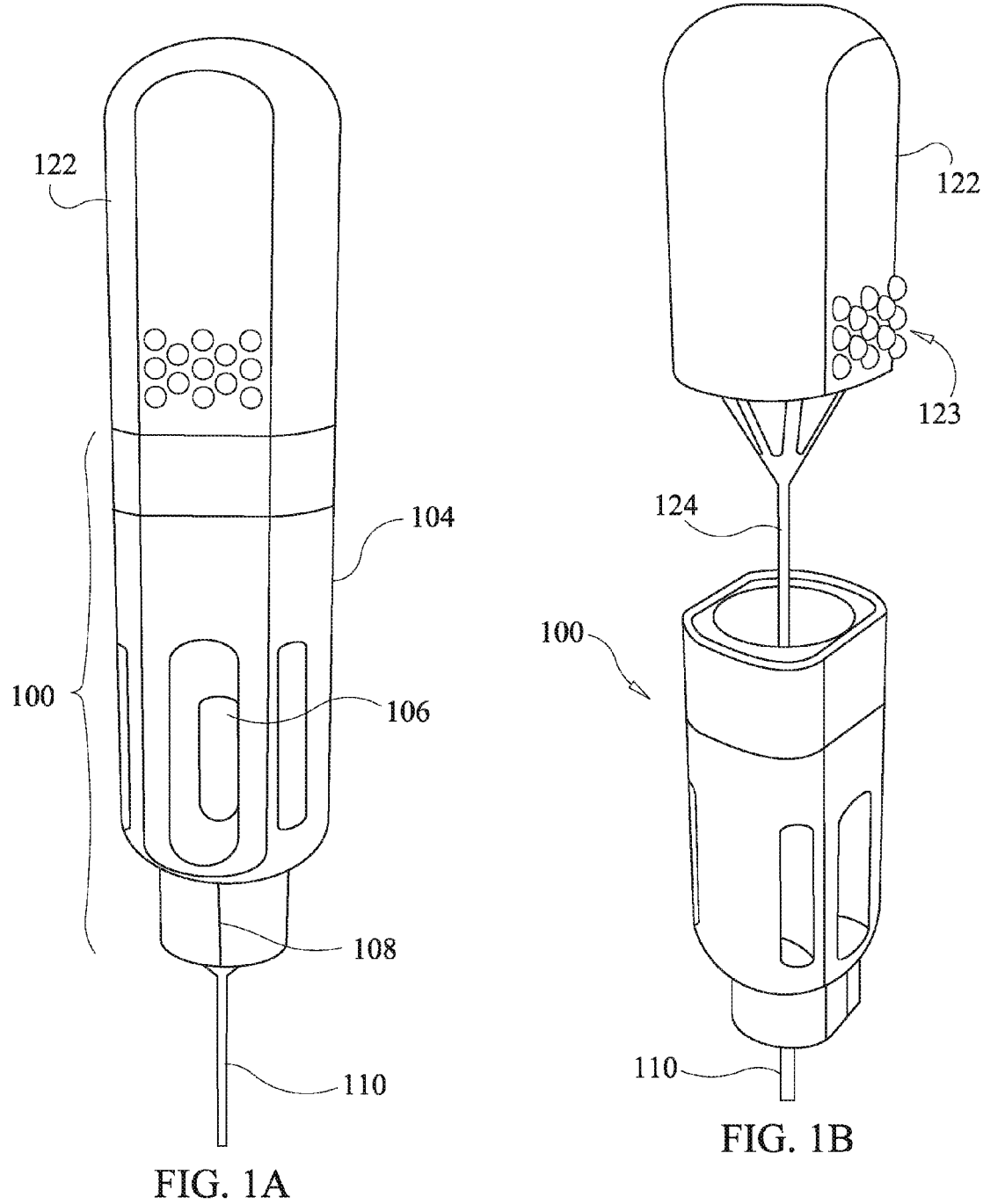
Figure 1C:
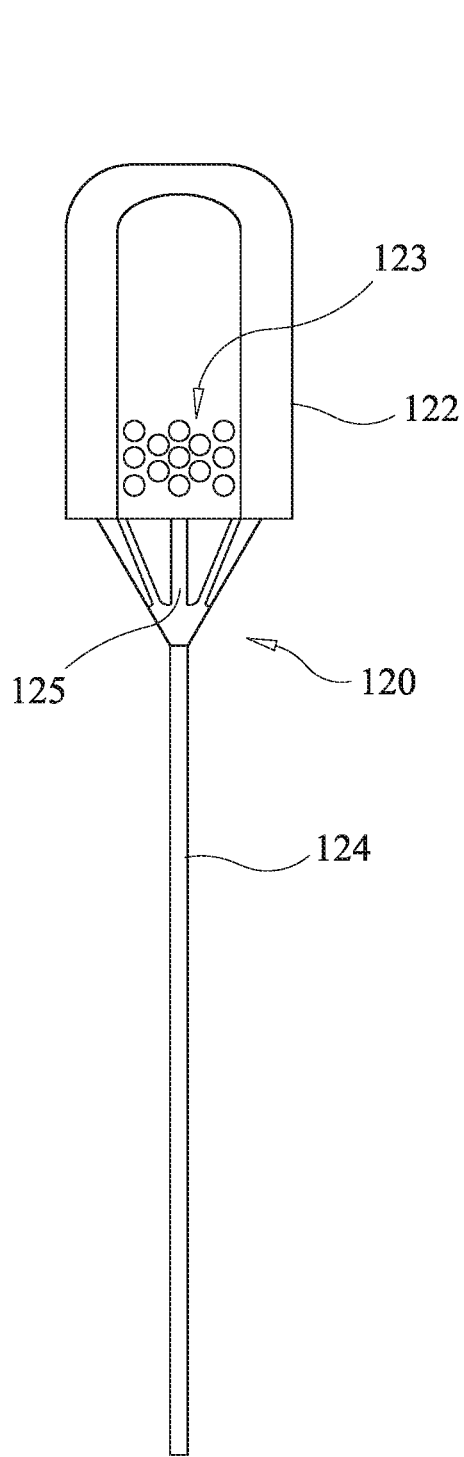
Figure 1D:
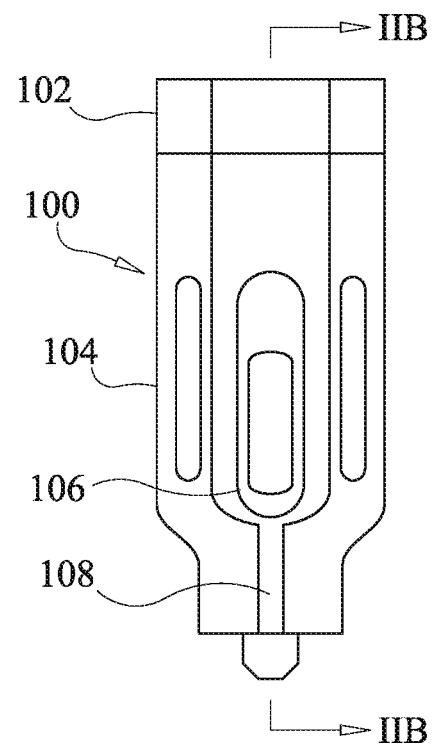
Figure 1E:
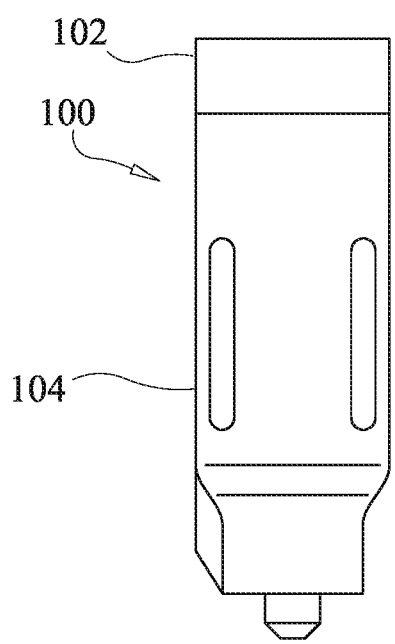

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to various embodiments of the present disclosure, examples of which are illustrated in the accompanying drawings. While the embodiments of the present disclosure will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New drug delivery devices, which can easily allow the accurate and precise implantation of multiple drug depots with minimal physical and psychological trauma to a patient are provided. In various embodiments the drug delivery device allows the user to dispense multiple drug depots, in sequence, to a site beneath the skin of the patient.

An optional feature of the drug delivery device of the present disclosure is that it allows the user to dispense multiple doses of the drug in sequence.

Another optional feature is that various embodiment include occluding devices that prevent drug depots from inadvertently being dislodged from the drug delivery device.

Still another feature optionally provided in various embodiments is a viewing aperture permitting visual confirmation of a number and type of drug depots after loading of the drug depots into the drug delivery device.

Yet another optional feature of various embodiments of the drug delivery device is a funnel body facilitating loading of small drug depots which are difficult to manually manipulate into small apertures.

A further optional feature of various embodiments of the drug delivery device is an indicia ring which includes either or both of alphanumeric labeling or color coding to facilitate selection of a drug delivery device containing the correct drug.

First Embodiment

Referring to FIGS. 1a-1e, a first embodiment of a drug delivery device of the present disclosure is shown comprising a housing 100, a cannula 110, and a plunger 120. The plunger has a knob 122 with an optional raised surface pattern 123 and a push rod 124. The raised surface pattern provides for tactile grip of the knob 122. The illustrated raise surface pattern is merely exemplary, and various modified patterns may be used. The housing 100 comprises a housing body 104 and a funnel body 102.

The housing body 104 optionally defines a viewing aperture 106 configured to allow viewing of a drug cartridge (discussed below) within the housing body 104 so as to confirm presence of drug depots. The viewing aperture 106 is sized to permit viewing of multiple drug depots loaded into the drug cartridge.

In various embodiments of the drug delivery device the cannula 110 has a proximal end engaged to the housing via a coupling device which is optionally embodied as, inter alia, a luer lock, threading fitting, friction fit fitting, or another fitting mechanism allowing the cannula 110 to functionally couple to the housing 100 so as to permit passage of a drug depot through the cannula 110 via entry at the proximal end and exit at a distal end. In various embodiments, the cannula 110 is hollow having a sufficient diameter to allow passage of the drug depot and the push rod 124 that facilitates delivery of the drug to the designated site beneath the skin. The distal end of the cannula 110 is capable of insertion to a site beneath the skin. The size of the cannula is dictated by the procedure.

Figure 2A:
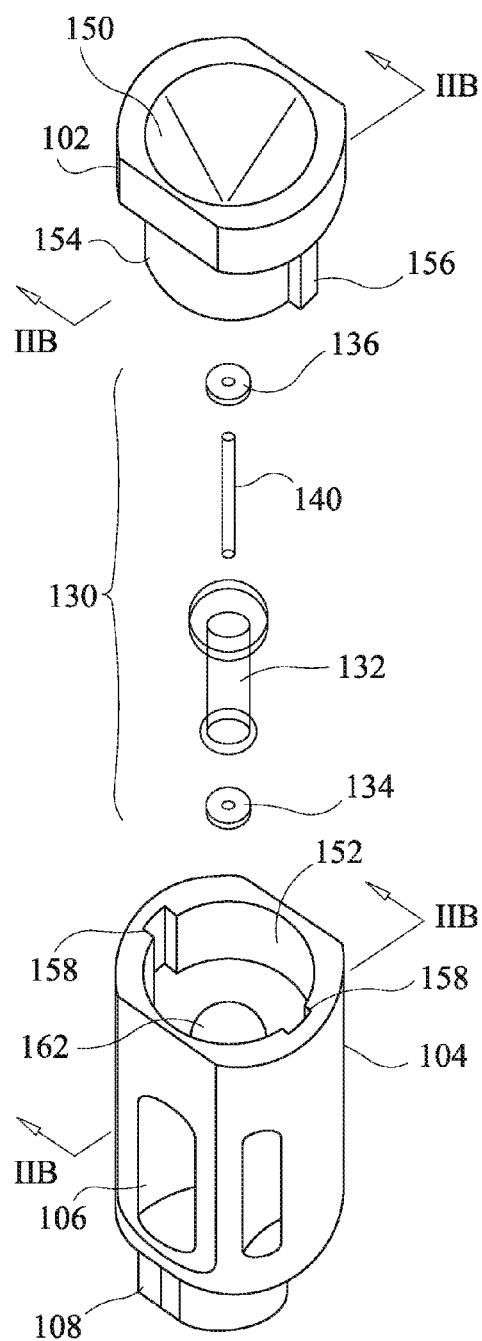
FIG. 2a is an exploded front, right side, top perspective view of the housing of FIG. 1e.
Figure 2B:
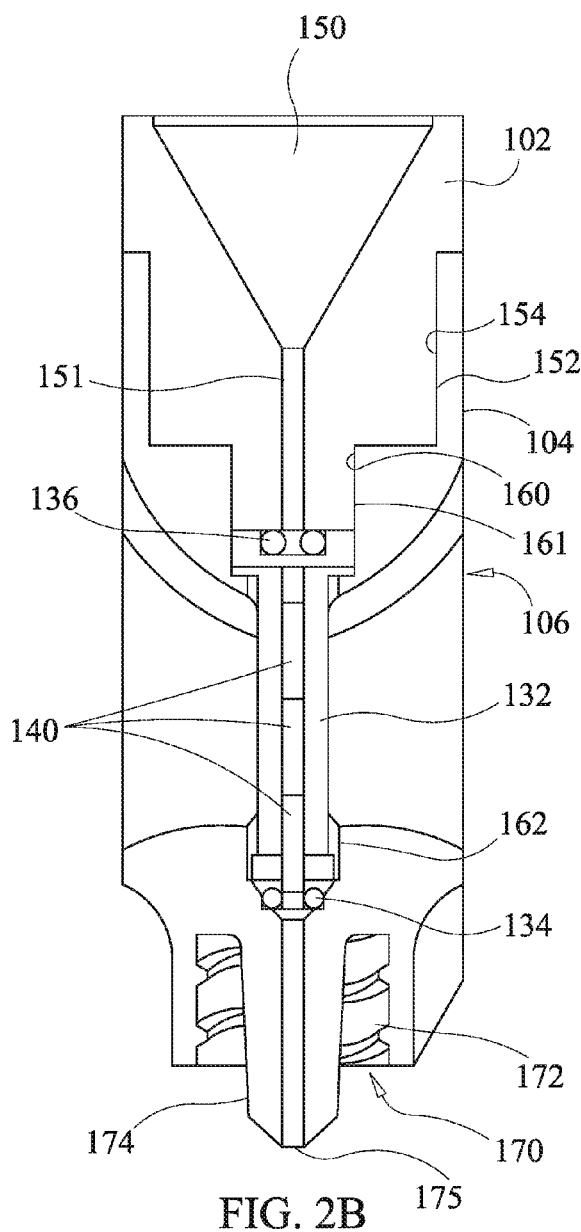
FIG. 2b is a cross-sectional view of the housing of FIG. 1d.

Referring to FIGS. 2a and 2b, internal construction of the housing 100 is shown along with an embodiment of a first drug cartridge 130. The first drug cartridge 130 is shown in an exploded view in FIG. 2a and comprises a cartridge tube 132, and proximate and distal O-rings, 136 and 134. The cartridge tube 132 is optionally dimensioned to accept multiple drug depots.

The first drug cartridge 130 is inserted into a receiving channel 162 of the housing body 104 with the proximal and distal O-rings, 136 and 134, respectively disposed at proximal and distal ends of the cartridge tube 132 as shown in the cross-sectional view of FIG. 2b. Drug depots 140 are disposed in the cartridge tube 132 and retained in the cartridge tube 132 by virtue of the proximal and distal O-rings, 136 and 134, having an internal diameter which is slightly less than an external diameter of the drug depots 140. For the purposes of the present disclosure in this respect, "slightly less" is intended to an amount small enough that, upon force being applied to the drug depots 140 by the push rod 124, the distal O-ring 134 will stretch radially outward due to force applied by the drug depots 140 to permit passage of the drug depots 140 therethrough without damage to the integrity of the drug depots 140. The first drug cartridge 130 is preferably formed of a clear or translucent material to permit viewing of the drug depots 140 via the viewing aperture 106 when the first drug cartridge 130 is installed in the housing body 104 as shown in FIG. 2b.

The funnel body 102 has a funnel bore 150 which has a funnel taper at the proximal end and transitions to a tubular configuration 151 opening at a distal end in alignment with the proximate O-ring 136. The funnel body 102 has a stepped configuration with a first step portion 154 and a second stepped portion 160 which respectively fit into a stepped recess of the housing body 140 comprising a first recess opening 152 and a second recess opening 161. The first step portion 154 has key ridges 156 (one visible in FIG. 2a with asymmetric opposing key ridge on the far side) which fit into key channels 158 defined in a wall of the first recess opening 152. The dimensioning of the key ridges 156 and key channels 158 is optionally configured to provide for a press fit of the funnel body 102 into the housing body 104. An alternative coupling mechanism for fixing the funnel body 102 to the housing body 104 may be employed such as threading, adhesives, clips, or a cantilevered arm snap catch as discussed below with reference to other embodiments of the present disclosure. The funnel bore 150 provides for ease of insertion of the push rod 124 of the plunger 120 as the funnel taper guides a distal end of the push rod 124 into the tubular configuration 151 of the funnel bore 150 upon insertion by a user. The funnel taper also guides drug depots 140 into the tubular configuration 151 when the drug delivery device is breach loaded.

The housing body 104 shown has an exemplary embodiment of the coupling device for connecting the cannula 110 comprising a nipple portion 174 defining a nipple channel 175 which is in alignment with the distal O-ring 134 so as to permit passage of the drug depots 140 therethrough and into the cannula 110 (shown in FIG. 1a), and a coupling bore 170 with an internal thread 172 for attachment of the cannula 110 via a luer lock mechanism known in the art. As noted above, the embodiments of the present disclosure is not limited to such a coupling device, and it is considered to be within the scope and spirit of the present disclosure to modify the housing body 104 as may be required to adapt other coupling devices.

The drug depots 140 are optionally loaded into the cartridge tube 130 during assembly of the first drug cartridge 130 into the housing body 104 and prior to placement of the proximate O-ring 136 and closure with the housing 100 with the funnel body 102. Such an operation is carried out by first installing the distal O-ring 134 into a bottom of the receiving channel 162 followed by installing the cartridge tube 132 into the receiving channel 162 such that a bottom of the cartridge tube 132 contacts or is proximate to the distal O-ring 134. Next, one or more of the drug depots 140 are inserted into the cartridge tube 132 via the proximate end thereof. Following insertion of the drug depots 140, the proximate O-ring 136 is installed followed by press fitting of the funnel body 102. Alternatively, the drug depots 140 may be breach loaded into the first drug cartridge 130 after assembly of the housing 100 including installation of the first drug cartridge 130. Using breach loading the drug depots 140 are disposed into the funnel bore 150 so that they are guided into the tubular configuration 151 of the funnel bore 150 by the funnel taper. Once in the tubular configuration 151 the drug depots 140 fall to the proximate O-ring 136 which restricts further falling. The push rod 124 of the plunger 120 is then used to push the individual ones of the drug depots 140 through the aperture of the proximate O-ring 136, expanding the proximate O-ring 136 in the process, and into the cartridge tube 132 whereat the drug depots 140 are retained by the proximate and distal O-rings, 136 and 134, until use.

Administration of the drug depots 140 is effected by first engaging the cannula 110 via the coupling device of the housing body 104. As an example without limitation in the illustrated embodiment, a luer lock coupling is used which engages the internal thread 172 of the coupling bore. An indicator ridge 108 is optionally provided on the housing body 104 such that when proper coupling of the luer lock is made, a corresponding ridge on a luer lock portion of the cannula 110 aligns with the indicator ridge 108 of the housing body 104. Prior to disposing the drug depots 140 in the patient, the user visually confirms presence of a correct number and type of the drug depots 140 via the viewing aperture 106 and the transparent body of the cartridge tube 132. Next, the cannula is inserted into the patient to place the tip of the cannula 110 at a desired location for disposition of the drug depots 140. Then the push rod 124 of the plunger 120 is inserted into the funnel bore 150 and on through the first drug cartridge 130, the housing body 104, and the cannula 110, so as to push the drug depots 140 out of the cannula 110 at the desired disposition location in the patient.

Second Embodiment

Figure 3A:
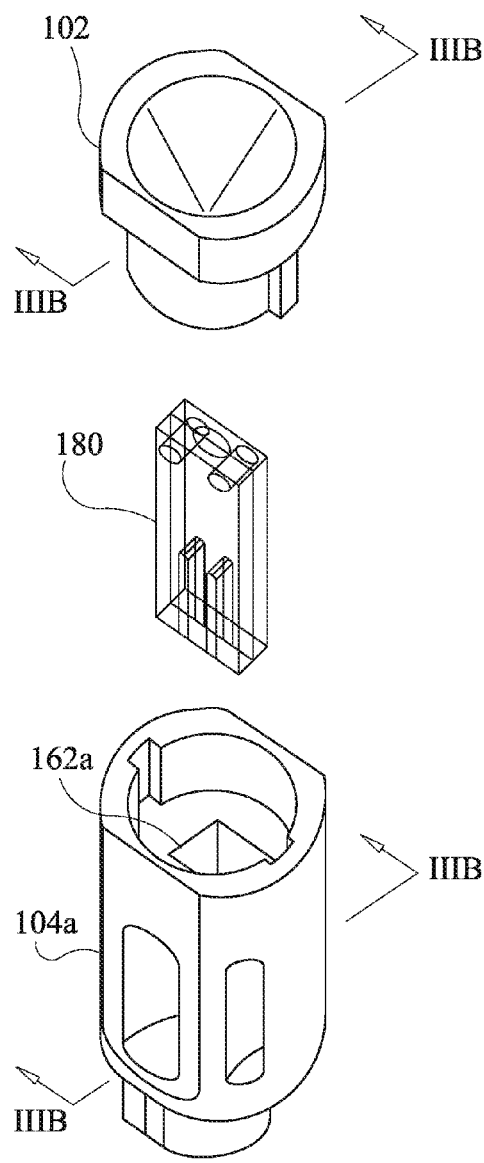
FIG. 3a is an exploded front, right side, top perspective view of a housing of a second embodiment of the drug delivery device of the present disclosure.
Figure 3B:
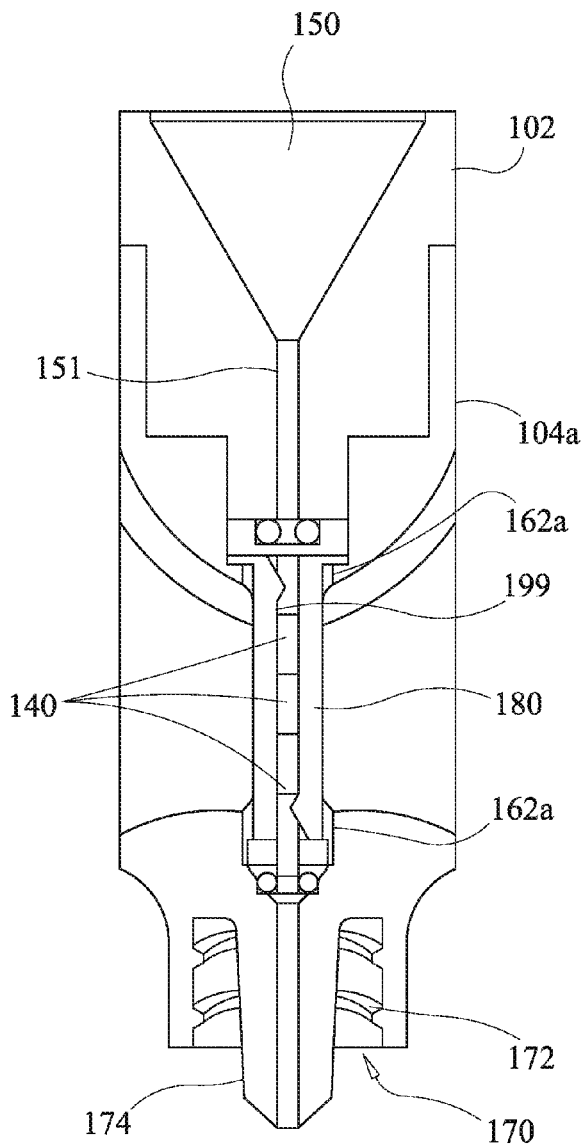
FIG. 3b is a cross-sectional view of the housing of FIG. 3a in an assembled state.

Referring now to FIGS. 3a-3c, a second embodiment of the drug delivery device of the present disclosure is shown, which is the same as the first embodiment except as related herein. Components substantially corresponding to those of the first embodiment, yet modified, are identified by like reference numerals with an alphabetic character appended thereto in order to facilitate an understanding of the relationships of the embodiments of the present disclosure. Components which are the same as in prior described embodiments have the same reference designators and further description thereof is omitted unless required to describe cooperation with modified components.

A second drug cartridge 180 is used in place of the first drug cartridge 130 and is inserted into a second receiving channel 162a of a second housing body 104a. The second receiving channel 162a is rectangular in cross section while the first receiving channel 162 is circular. The second drug cartridge 180 comprises first and second plates, 182 and 184, respectively having first and second cantilever arms, 194 and 196, with corresponding ramped protrusions, 195 and 197, at distal ends thereof with proximate ends thereof acting as fixed cantilever mounts. The first and second plates, 182 and 184, each have a half channel, 190 and 192, extending from an end of a respective plate along a body of the respective plate and a corresponding one of the cantilever arms, 194 and 196, up to a corresponding one of the ramped protrusions, 195 and 197. Optionally, the first and second plates, 182 and 184, are formed identically to reduce manufacturing and assembly costs. The first and second plates, 182 and 184, each have bosses 186 and corresponding boss receiving holes 188. The first and second plates, 182 and 184, are fitted together as illustrated in FIG. 3c, with bosses 186 fitting into opposing boss receiving holes 188. Optionally, the bosses 186 and boss receiving holes 188 are dimensioned to provide a press fit facilitating retention of the first and second plates, 182 and 184, to each other. Alternative means of securing the first and second plates, 182 and 184, may be used such as adhesives, clips, molded snap latches, or other means known to those skilled in the art.

When the first and second plates, 182 and 184, are assembled together, the half channels, 190 and 192, align together and define a depot channel 199 for receipt of the drug depots 140 as shown in FIG. 3b. The ramped protrusions, 195 and 197, each at least partially occlude the depot channel to an extent sufficient to prevent the drug depots 140 from falling out of the second drug cartridge 180 via either one of ends of the depot channel 199. Material selection and dimensioning of the cantilever arms, 194 and 196, are sufficient to provide a spring constant allowing deflection of the cantilever arms by force of the drug depots being urged through the funnel channel bore 150 and the depot channel 199 by the push rod 124 of the plunger 120 without comprise of the integrity of the drug depots 140.

Preferably, although not required, the first and second plates, 182 and 184, are formed of clear or transparent material to permit visual confirmation of the number and type of the drug depots 140 loaded in the second drug cartridge 180 via the viewing aperture 106. As in the case of the first drug cartridge 130, the drug depots 140 may be loaded into the second drug cartridge 180 either during assembly or post assembly by breach loading.

While in the illustrated embodiment of the second drug cartridge 180 the first and second plates, 182 and 184, are identical, this is not a requirement of the present disclosure. Alternatively, one of the plates may include both of the cantilever arms, 194 and 196, while another one of the plates defines a continuous half channel. Likewise, the bosses 186 and receiving holes 188, may be redistributed among the plates with all bosses or all boss receiving holes on one plate and with all receiving holes or all bosses on another one of the plates. Other configurations of the plates may be effected which provide for the retention of the drug depots 140 such as providing an elastically biased occlusion of a depot channel by means of elastomeric buttons, coils springs, fuzz balls formed of plastic, elastic foam material, flexible fibers, or biased beveled end pins, which are merely examples of other retention devices and not considered limiting.

The drug depots 140 are optionally loaded into the second drug cartridge 180 during assembly of the second drug cartridge 180 and prior to placement of the second drug cartridge 180 into the housing body 104a and closure with the funnel body 102. Such an operation is carried out by placement of one or more of the drug depots into the half channel 192 of the second plate 184. Next, the first plate 182 is pressed into place over the second plate 184. Then, the assembled second drug cartridge 180 is installed into the receiving channel 162a and the funnel body 102 is pressed into place. Alternatively, the drug depots 140 may be breach loaded into the second drug cartridge 180 after assembly of the housing 100 including installation of the second drug cartridge 180. Using breach loading the drug depots 140 are disposed into the funnel bore 150 so that they are guided into the tubular configuration 151 of the funnel bore 150 by the funnel taper. Once in the tubular configuration 151 the drug depots 140 fall into the second drug cartridge 180 up to a first of the ramped protrusions, 195 and 197, encountered. The push rod 124 of the plunger 120 is then used to push the drug depots 140 past the first of the ramped protrusions, 195 and 197, encountered, deflecting a corresponding one of the first and second cantilever arms, 194 and 196, in the process, to permit passage of the drug depot into the depot channel formed by the first and second half channels, 190 and 192, to a position between the first and second ramped protrusion, 195 and 197. The drug depots 140 are retained until use in the second drug cartridge 180 by the first and second ramped protrusions, 195 and 197, occluding the depot channel.

Administration of the drug depots 140 is effected by first engaging the cannula 110 via the coupling device of the housing body 104a and the cannula 110, as in the example of the first embodiment, a luer lock coupling is used which engages the internal thread 172 of the coupling bore. An indicator ridge 108 is provided on the housing body 104 such that when proper coupling of the luer lock is made, a corresponding ridge on a luer lock portion of the cannula 110 aligns with the indicator ridge of 108 of housing body. Prior to disposing the drug depots 140 in the patient, the user visually confirms presence of a correct number and type of the drug depots 140 via the viewing aperture 106 and the transparent body of the second drug cartridge 180. Next, the cannula 110 is inserted into the patient to place the tip of the cannula 110 at a desired location for disposition of the drug depots 140. Then the push rod 124 of the plunger 120 is inserted into the funnel bore 150 and on through the second drug cartridge 180, the housing body 104a, and the cannula 110, so as to push the drug depots 140 out of the cannula 110 at the desired disposition location in the patient.

Third Embodiment

Referring now to FIGS. 4a-4e, a third embodiment of the of the drug delivery device of the present disclosure having a partially integrated drug cartridge and a ring member is shown which is the same as prior described embodiments except as related herein. Components substantially corresponding to those of the second embodiment, yet modified, are identified by like reference numerals with an alphabetic character appended thereto in order to facilitate an understanding of the relationships of the embodiments of the present disclosure. Components which are the same as in prior described embodiments have the same reference designators and further description thereof is omitted unless required to describe cooperation with modified components.

In FIG. 4a an exploded view of the third embodiment of the present disclosure is shown wherein a third housing body 104b is configured to accept installation of a first ring member 210, and a second funnel body 102b having the partially integral drug cartridge comprised of first cartridge plate 200 and second cartridge plate 202. The second cartridge plate 202 is formed integrally with a funnel portion of the second funnel body 102b. The first cartridge plate 200 snaps onto the second cartridge plate 202 by means of cantilever catch hook arms 208 engaging a distal end of the first cartridge plate 200, as shown in FIG. 4d, while a proximate end of the first cartridge plate 200 is engaged with hinging apertures 204 of the second funnel body 102b. Assembly of the third embodiment is accomplished by snapping the first cartridge plate 200 onto the second cartridge plate 202, sliding the first ring member 210 to engage an upper portion of the second funnel body as shown in FIG. 4b, followed by sliding the second funnel body 102b into engagement with the third housing body 104b thereby completing assembly of a third housing 100c as shown in FIGS. 4c and 4e.

As illustrated in FIG. 4e, the first ring member 210 has a bottom edge contacting a top ledge 254 of the third housing body 104b and has a top edge extending to an end of the third housing 100c and preferably surrounding the upper portion of the second funnel body 102b. surrounding the upper portion of the funnel body 102b renders tapering with the assembled third housing 104b difficult because disassembly requires that the second funnel body 102b be forcibly separated from the housing body 104c and a lack of an exposed periphery of the second funnel body 102b inhibits an ability of one to firmly grasp the second funnel body 102b.

When the plunger 120 is fully inserted, the plunger knob 122 is adjacent the first ring member 210. Optional selection of different colors for the plunger knob 122 and the first ring member 210 provides contrast when the plunger 120 is fully inserted facilitating visual confirmation that the plunger 120 is fully inserted.

Figure 5A:
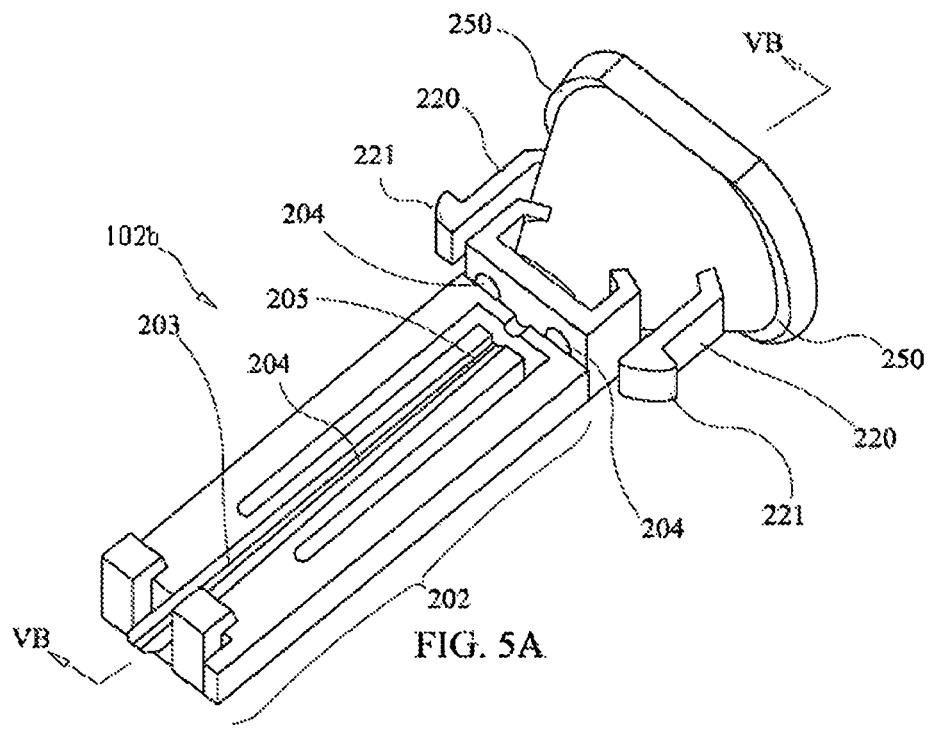
FIG. 5a is a front, right side, and bottom perspective view of a funnel body having an integral second drug cartridge plate of the third embodiment of a drug delivery device of the present disclosure.
Figure 5B:
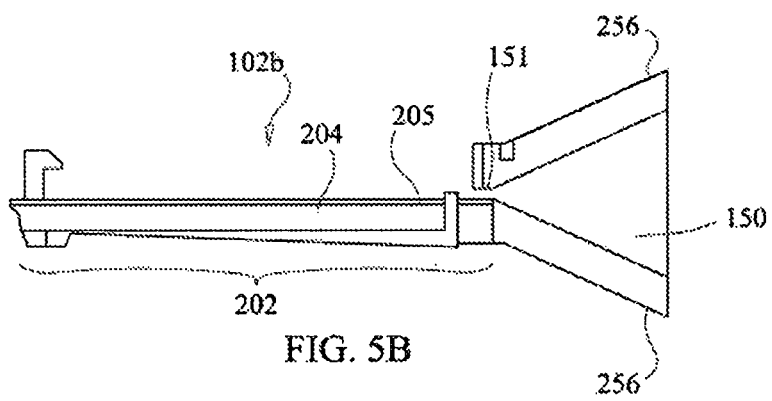

Referring to FIGS. 5a and 5b, the second funnel body 102b has the second cartridge plate 202 molded integrally therewith. A third cantilever arm 204, having a ramped protrusion 205, is formed in the second cartridge plate 202 by a defining aperture in the second cartridge plate 202. A first half depot channel 203 extends the length of the second cartridge plate 202, with the exception of the ramped protrusion 205 and the defining aperture, and communicates with the tubular configuration 151 of the funnel bore 150. Cantilever catch arms 220, having catch hook protrusions 221, are provided on opposing sides of the second funnel body for engaging with the third housing body 104b as described below.

Figure 5C:
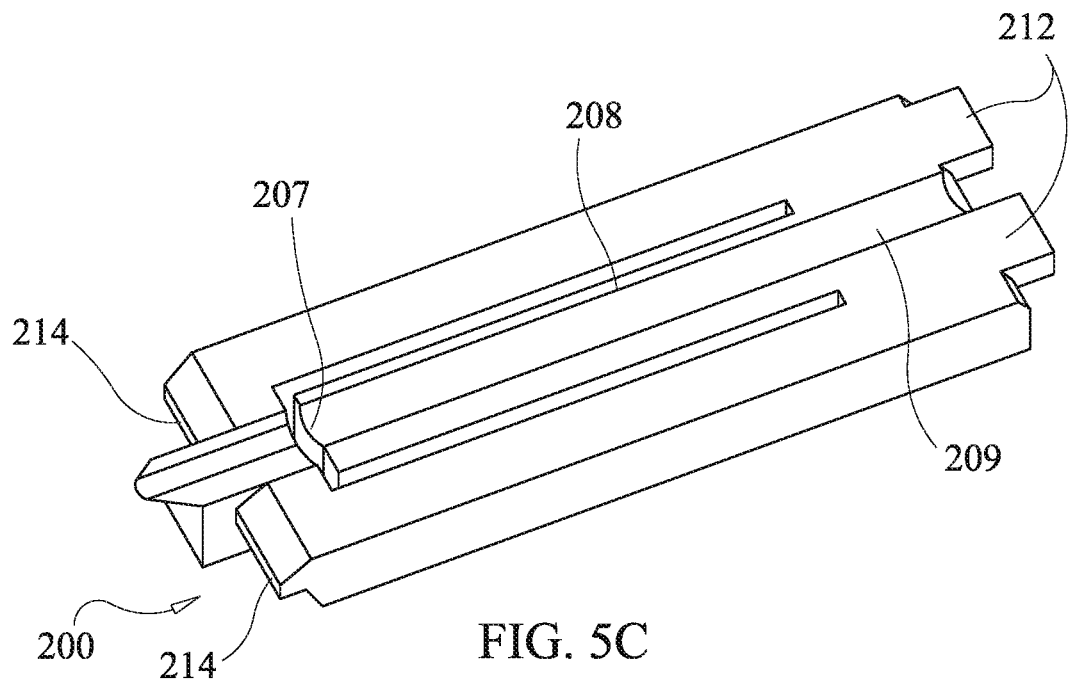
FIG. 5c is a front, right side, and bottom perspective view of a first drug cartridge plate of the third embodiment of a drug delivery device of the present disclosure.
Figure 5D:
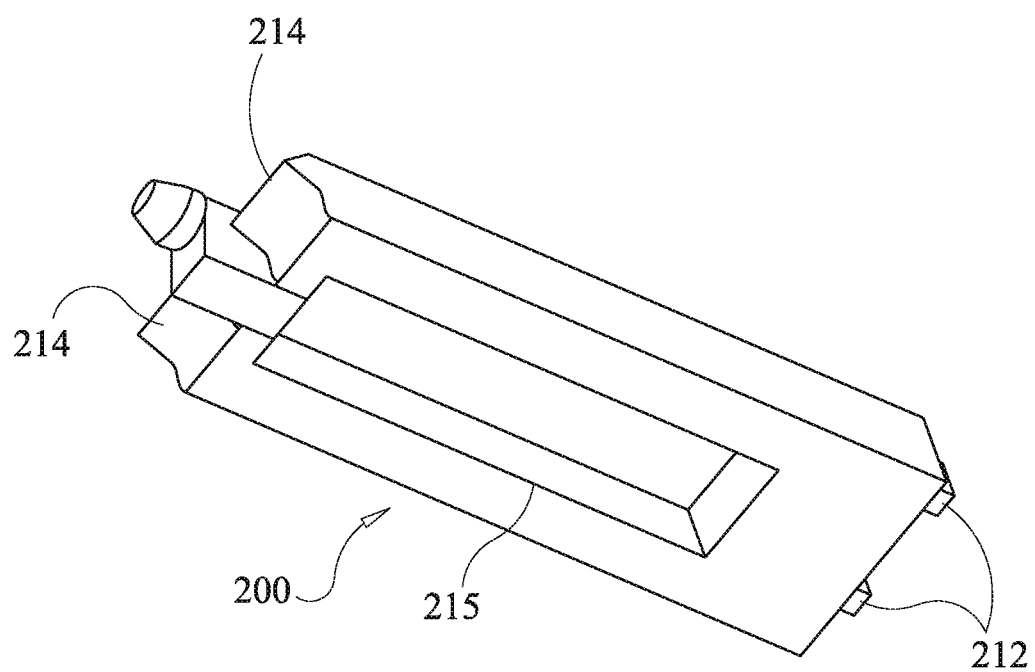
FIG. 5d is a back side, right side, and bottom perspective view of the first drug cartridge plate of FIG. 5c.
Figure 6A:
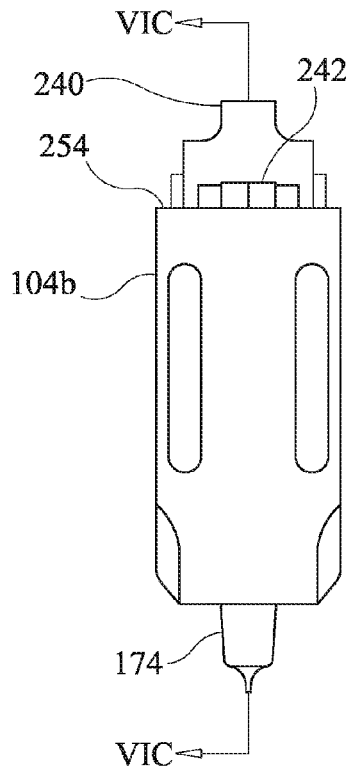
FIG. 6a is a right side elevation view of a housing body of the third embodiment of a drug delivery device of the present disclosure.
Figure 6B:
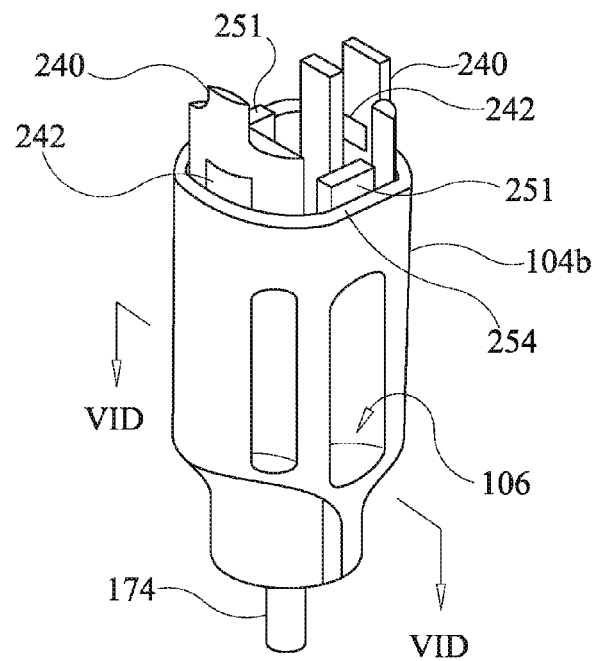
Figure 6C:
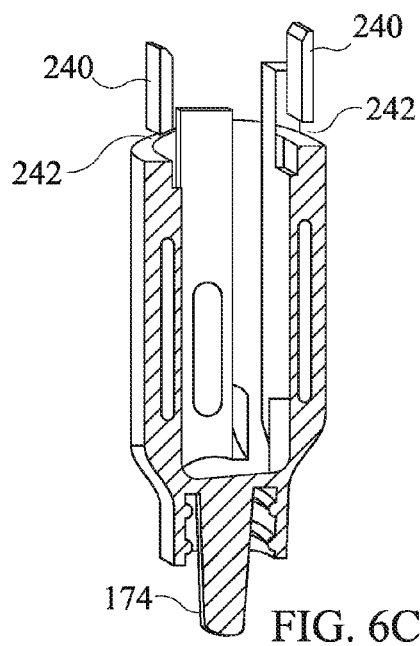
FIG. 6c is a cross-sectional view of the housing body of FIG. 6a taken along a longitudinal direction of the housing body.
Figure 6D:
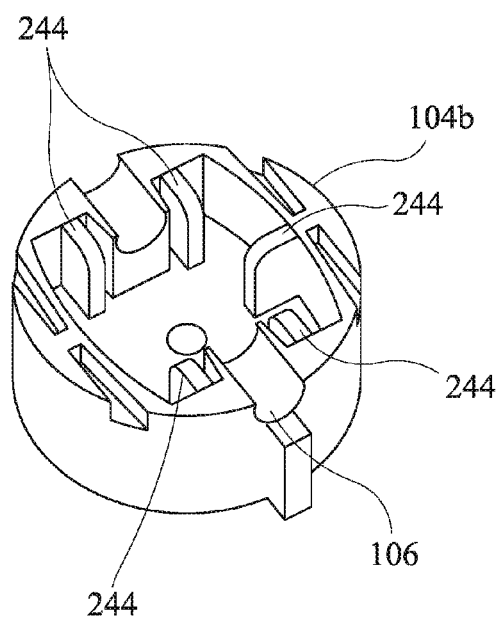
FIG. 6d is a cross-sectional view of the housing body of FIG. 6a taken along a lateral direction of the housing body.

Referring to FIGS. 5c and 5d, the first cartridge plate 200 has a fourth cantilever arm 208, having a ramped protrusion 207, formed in the first cartridge plate 202 by a defining aperture. A second half depot channel 209 extends the length of the first cartridge plate 200, with the exception of the ramped protrusion 207 and the defining aperture, and communicates with the tubular configuration 151 of the funnel bore 150. Hinging protrusions 212 are provided at a proximate end of the first cartridge plate 200 and are configured to engage the hinging apertures 204 of the second funnel body 202. Hook engaging protrusions 214 are provided at a distal end of the first cartridge plate 200 and are configured to engage the cantilever catch hook arms 208 of the second cartridge plate 202. A bevel on the hook engaging protrusions 214 slidably engages a bevel on the cantilever catch hook arms 208 to impart lateral force to the cantilever catch hook arms 208 to deflect the cantilever catch hook arms 208 when the first cartridge plate 200 is snapped into position on the second cartridge plate 202. It will be realized by those skilled in the art in view of this disclosure that the positioning of the cantilever catch hook arms 208 and the hook engaging protrusions 214 may be interchanged. Additionally, other methods may be employed to engage the first and second cartridge plates, 200 and 202, with each other and adaptation of other engagement methods is considered to be within the scope and spirit of the present disclosure.

As shown in FIG. 5d, a rectangular recess 215 is provided in a side of the first cartridge plate 200 opposite that of the second half depot channel 209 and the fourth cantilever arm 208. The rectangular recess 215 provides for thinning of the fourth cantilever arm 208 to adjust its spring coefficient to provide a sufficient biasing force permitting passage of the drug depots 140 without damaging the integrity thereof, as discussed previously in relation to the second embodiment of the present disclosure. As in the cases of the first and second drug cartridges, 130 and 180, the drug depots may be loaded into the partially integrated second drug cartridge either during assembly or post assembly by breach loading.

Preferably, although not required, at least one, and more preferably both the first cartridge plate 200 and the second cartridge plate 202 are formed of clear or transparent material to permit visual confirmation of the number and type of the drug depots 140 loaded in the partially integrated drug cartridge via the viewing aperture 106. As in the case of the first and second drug cartridges, 130 and 180, the drug depots 140 may be loaded into the second drug cartridge 180 either during assembly or post assembly by breach loading.

Referring to FIGS. 6a-6d, an embodiment of a configuration of the third housing body 104b of FIGS. 4a-4e is shown. While similar to the embodiment of the second housing 104a, the third housing body 104 has a mating configuration for engagement of the second funnel body 102b different from the press fit engagement that the second housing body 104a has for engaging the funnel body 102. Instead, the third housing body 104b has piers 251 and stanchions 240, with each of the stanchions 240 including a snap engagement aperture 242. Additionally, the third housing body 104b has buttresses 244, shown in FIG. 6d, arranged to accept a distal end of the integral drug cartridge of the second funnel body 102b instead of the second receiving channel 162a of the second housing body 104a. Alternatively, the buttresses 244 may be replaced with solid material defining an aperture configured to accept the distal end of the integral drug cartridge as in the case of the receiving channels 162 and 162a of the first and second embodiments.

Figure 7A:
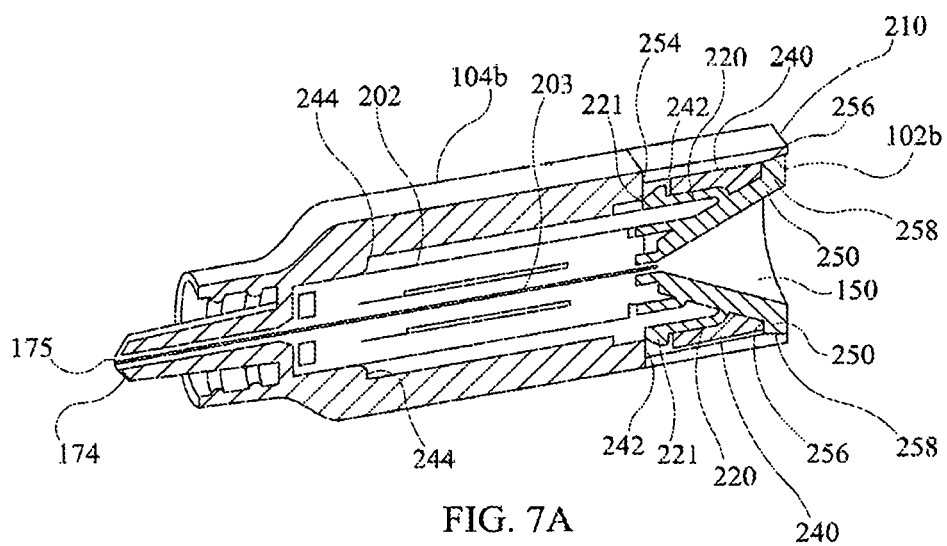
FIG. 7a is a cross-sectional perspective view of the assembled housing of the third embodiment of a drug delivery device of the present disclosure.
Figure 7B:
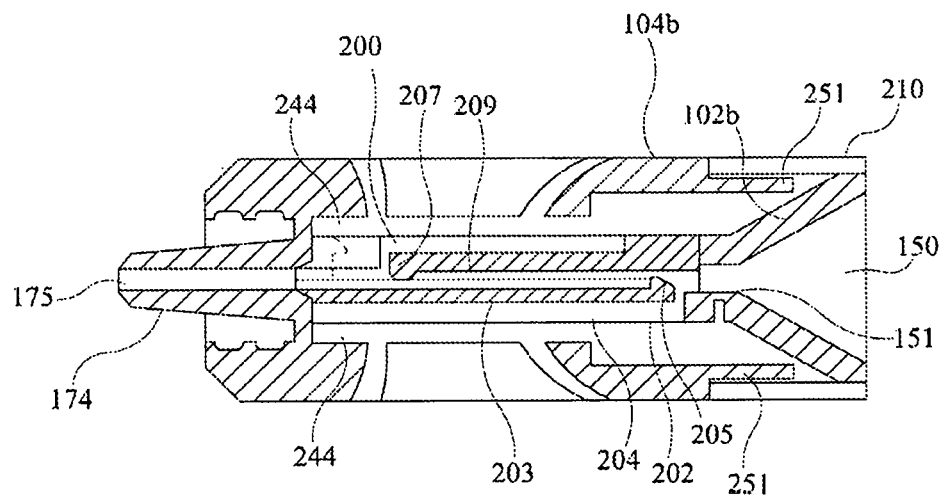
FIG. 7b is a cross-sectional view of the assembled housing of the third embodiment of a drug delivery device of the present disclosure.

Referring to FIGS. 7a and 7b, orthogonal cross sections of the third embodiment of the present disclosure are shown detailing the mechanical engagement of the third housing body 104b, the first ring member 210, and the second funnel body 102b having the partially integral drug cartridge. The first cartridge plate 200 is snapped into engagement with the second cartridge plate 202 via the cantilever catch hook arms 208 and the hinging protrusions 212 (not shown). The distal end of the partially integral drug cartridge is retained in position by the buttresses 244.

The second funnel body 102b is secured in the third housing body 104b by means of the cantilever catch arms 220 and the catch hook protrusions 221 respectively engaging the stanchions 240 and the snap engagement apertures 242. Additionally, the second funnel body 102b has flanges 250 which seat on ends of the stanchions 240 in cooperation with the engagement of the cantilever catch arms 220 thereby securing the second funnel body 102b in a longitudinal direction of the third housing body 104b. The first ring member 210 is secured in the longitudinal direction between a ledge 254 of the third housing body 104b and inclined faces 256 of the second funnel body 102b, which engage corresponding inclined faces 258 of the first ring member 210.

The drug depots 140 are optionally loaded into the partially integral drug cartridge during assembly of the partially integral drug cartridge 180 and prior to placement of the partially integral drug cartridge 180 into the housing body 104a and closure with the funnel body 102. Such an operation is carried out by placement of one or more of the drug depots into the half channel 192 of the second plate 184. Next, the first plate 182 is pressed into place over the second plate 184. Then, the assembled partially integral drug cartridge is installed into the housing body 104b and the funnel body 102b is pressed into place. Alternatively, the drug depots 140 may be breach loaded into the partially integral drug cartridge after assembly of the partially integral drug cartridge and installation thereof into the housing body 104b as shown in FIGS. 7a and 7b. Using breach loading the drug depots 140 are disposed into the funnel bore 150 so that they are guided into the tubular configuration 151 of the funnel bore 150 by the funnel taper. Once in the tubular configuration 151 the drug depots 140 fall into the partially integral drug cartridge down to the ramped protrusion 205. The push rod 124 of the plunger 120 is then used to push the drug depots 140 past the ramped protrusion 205, deflecting the third cantilever arm 204 in the process to permit passage of the drug depot into the depot channel formed by the first and second half channels, 203 and 209, to a position between the ramped protrusions, 203 and 209. The drug depots 140 are retained until use in the partially integral drug cartridge by the ramped protrusions, 203 and 209, occluding the depot channel.

Administration of the drug depots 140 is effected by first engaging the cannula 110 via the coupling device of the housing body 104b and the cannula 110, as in the example of the first embodiment, a luer lock coupling is used which engages the internal thread 172 of the coupling bore. An indicator ridge 108 is provided on the housing body 104 such that when proper coupling of the luer lock is made, a corresponding ridge on a luer lock portion of the cannula 110 aligns with the indicator ridge of 108 of housing body. Prior to disposing the drug depots 140 in the patient, the user visually confirms presence of a correct number and type of the drug depots 140 via the viewing aperture 106 and the transparent body of the partially integral drug cartridge. Next, the cannula 110 is inserted into the patient to place the tip of the cannula 110 at a desired location for disposition of the drug depots 140. Then the push rod 124 of the plunger 120 is inserted into the funnel bore 150 and on through the partially integral drug cartridge, the housing body 104b, and the cannula 110, so as to push the drug depots 140 out of the cannula 110 at the desired disposition location in the patient.

Fourth Embodiment

Figure 8C:
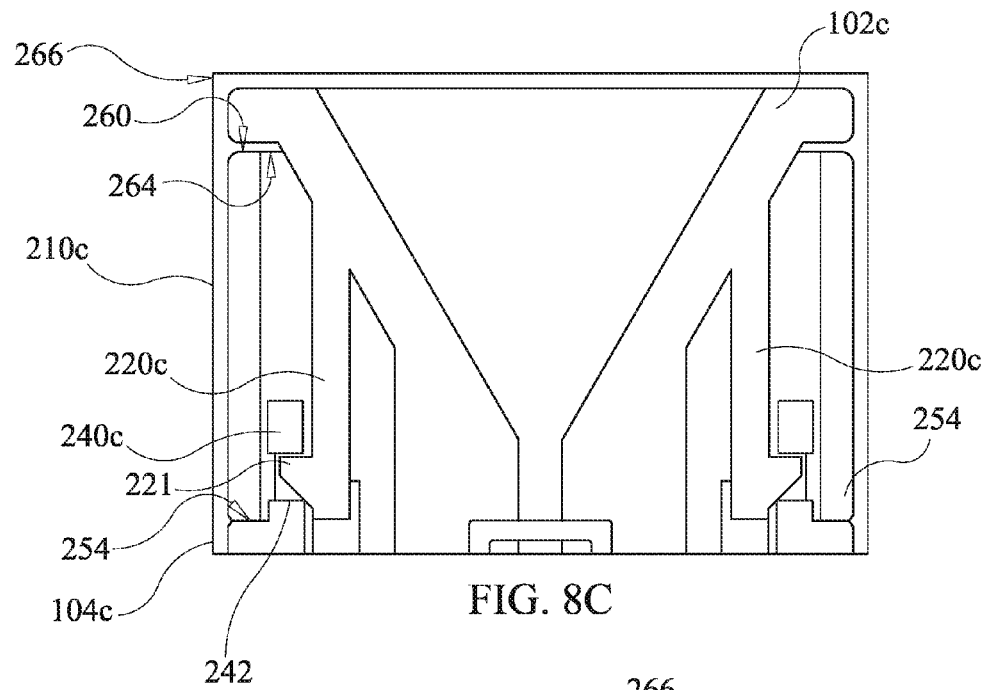
FIG. 8c is a cross-sectional partial view of the assembled housing of FIG. 8b.

Referring to FIGS. 8a-8c, a fourth embodiment of the present disclosure has an alternative ring member arrangement which entails variations of the first ring member 210, the second funnel body 102b, and the third housing body 104b of FIGS. 7a and 7b yielding a second ring member 210c, a fourth funnel body 102c, and a fourth housing body 104c. The fourth embodiment of the drug delivery device of the present disclosure is the same as prior described third embodiment except as related herein. In particular, the fourth embodiment provides an alternative ring member configuration to the ring member configuration of the third embodiment. Components substantially corresponding to those of the third embodiment, yet modified, are identified by like reference numerals with an alphabetic character appended thereto in order to facilitate an understanding of the relationships of the embodiments of the present disclosure. Components which are the same as in prior described embodiments have the same reference designators and further description thereof is omitted unless required to describe cooperation with modified components.

Figures 8D, 8E:
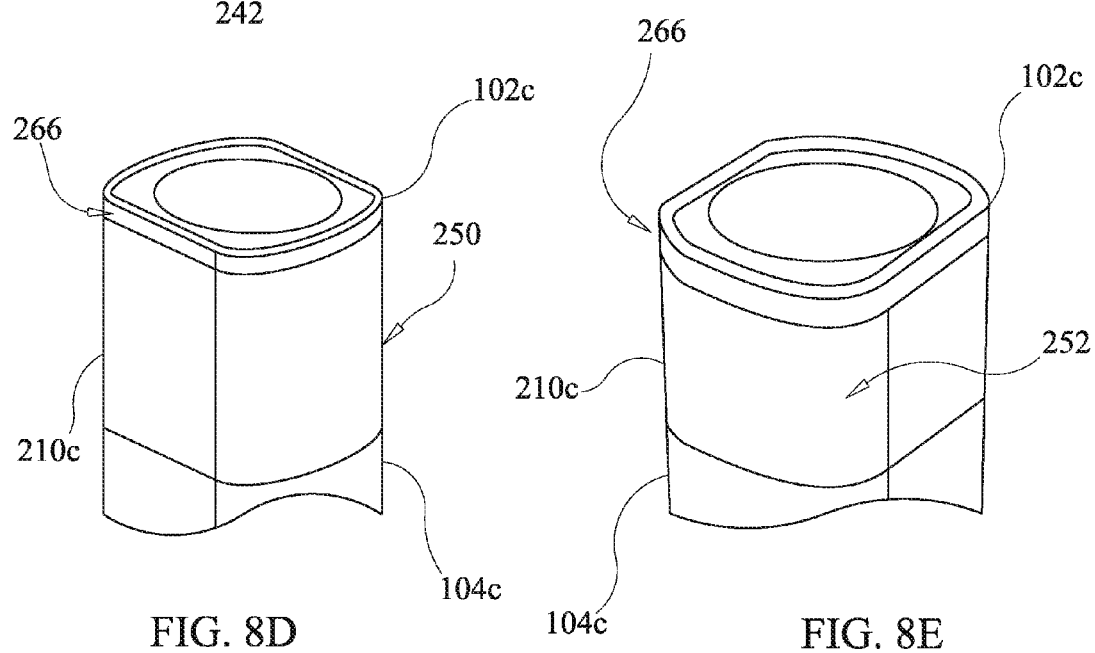
FIG. 8d is a right side, front side, and top side perspective view of the housing of FIG. 8a in an assembled state showing indicia.
FIG. 8e is a front side, right side, and top side perspective view of the housing of FIG. 8a in an assembled state showing indicia.

The fourth housing body 104c has a stanchion ring 104c defining snap engagement apertures 242c instead of the stanchions 240 of the third housing body 104b. The second ring member 210c lacks the inclined faces 258 of the first ring member 210 and instead has a wider ring end surface 260. The fourth funnel body 102c lacks the inclined surface 256 of the third funnel body and instead has a funnel flange 262 which forms an annular end surface wider than that of the third funnel body 102b and an outer peripheral surface 266. The funnel flange 262 has a flange under-face 264 which secures the second ring member 210c in the longitudinal direction in conjunction with the ledge 254 of the fourth funnel body 102c. The outer peripheral surface 266 remains exposed after assembly of the drug delivery device as shown in FIGS. 8b, 8d, and 8e. The fourth funnel body 102c has cantilever catch arms 220c which merely differ from those of the third funnel body 102b in lacking a bend at base ends thereof. As will be appreciated by those skilled in the art having benefit of the present disclosure, snap catches or latches, as described above, may be configured to interchange positions of the cantilever arm and catch hook with the position of the snap engagement aperture. The loading and use of the fourth embodiment of the drug delivery device is the same as for the third embodiment of the drug delivery device.

Indicia Features

Each of the third and fourth embodiments of the present disclosure comprises ring members which may be used for identification purposes. The first and second ring members, 210 and 210c, are optionally color coded and/or provided with indicia, 250 and 252, indicating, for example and without limitation, drug type, drug name, dosage, lot no., or expiration date. The provision of the indicia is shown in FIGS. 8d and 8e with relation to the second ring member 210 with the understanding that a similar indicia arrangement is also applicable to the first ring member 210. The use of either of the first or second ring members, 210 or 210c, permits the drug delivery device to be conveniently marked at time of assembly by choosing a ring member having the required indicia. Hence, other more complex components need only be stocked in generic configurations lacking indicia.

Modifications of Embodiments of the Drug Delivery Device.

A. Incorporation of Snap Latch in First and Second Embodiment.

The funnel body 102 of the first and second embodiment of the drug delivery device does not require use of a ring member and press fits into the housing body 104 or 104a. While the funnel body 102 is shown in a press fit configuration, it will be understood by those skilled in that art that the funnel body 102 is also modifiable to incorporate the cantilever catch arms, 220 or 220c, and the catch hook protrusions 221 of the third or fourth funnel bodies, 102b or 102c, while modifying the first or second housing body, 104 or 104a, to include the stanchions 240 or the stanchion ring 240c and the included snap engagement apertures, 242 or 242c.

B. Incorporation of Ring Member in First and Second Embodiment.

The present disclosure further includes embodiments wherein the ring members, 210 or 210c, are incorporated into either the first or second embodiments described above. Incorporation involves reducing an outer diameter of at least a portion of the funnel body 102 to accept the ring member, 210 or 210, in accordance with the corresponding configurations of the third or fourth funnel bodies, 102b or 102c. Alternatively, or in addition to the adjustment of the funnel body 102, a similar adjustment of the housing body 104 may also be made to accommodate either of the ring members 210 or 210c.

C. Incorporation of Press Fit in Third or Fourth Embodiment.

The present disclosure further includes embodiments of the drug delivery device wherein the third or fourth embodiments of the drug delivery device are modified to utilize a press fit of the funnel body into the housing body. The third and fourth embodiments detailed above utilize snap catches to engage the funnel bodies, 102b and 102c, with the housing bodies, 104b and 104c. In order to utilize a press fit engagement as used in the first and second embodiments, the cantilever catch arms, 220 or 220c, and the catch hook protrusions 221 of the second or third funnel bodies, 102b or 102c, may be replaced with a prong to engage in a press fit manner a groove or aperture in modified stanchions of the third or fourth housing bodies, 104 or 104a.

D. Incorporation of First and Second Drug Cartridges into the Third or Fourth Embodiments.

The present disclosure further includes embodiments of the drug delivery device wherein the third or fourth embodiments of the drug delivery device, having ring members and the partially integral drug cartridge, are modified to accept either of the first or second drug cartridges, 130 or 180, in place of the partially integral drug cartridge. The corresponding housing body, 104b or 104c, is modified to include engaging portions of the first or second housing body, namely to incorporate either the receiving channel 162 for the first drug cartridge 102 or the receiving channel 162a for the second drug cartridge 180. Similarly, the corresponding funnel body, 102b or 102c, is modified to eliminate the integral drug cartridge plate 202 and to extend the tubular configuration 151 of the funnel bore 150 to or proximate to the corresponding proximate end of the first or second drug cartridge 130 or 180.

E. Integral Incorporation of Drug Cartridges into the Housing.

The drug delivery device of the present disclosure further includes embodiments of the first through fourth above described embodiments wherein the drug cartridge of the respective embodiments is made integral with the housing body. Hence, unless expressly stated otherwise in the appended claims, integration of drug cartridge structure into a housing body is considered to be within the scope of the claims. Thus, claiming a housing body and a drug cartridge does not exclude the drug cartridge being integral with the housing body or parts thereof absent claim language to the contrary.

In the first embodiment the housing body 104 may be formed in first and second housing body halves which respectively incorporate first and second half depot channels which replace a depot channel defined by the cartridge tube 132. Cavities are defined by each of the first and second housing body halves which are configure to accept the proximal and distal O-rings 136 and 134.

In the second embodiment the housing body 104a may be formed in first and second housing body halves which respectively incorporate first and second half depot channels which replace a depot channel defined by the half channels of the first and second plates, 182 and 184. The first and second cantilever arms, 194 and 196, are optionally molded into the first and second housing body halves or attached by means known to those skilled in the art. Alternatively, the first and second cantilever arms, 194 and 196, are optionally replaced with deformable devices at positions corresponding to the first and second ramped protrusions, 195 and 197, and which are accepted in cavities defined by one or both of the first and second housing body halves.

In the third and fourth embodiments the housing body, 104b or 104c, may be formed in first and second housing body halves which respectively incorporate first and second half depot channels which replace a depot channel defined by the half channels of the first and second cartridge plates, 200 and 202. The third and fourth cantilever arms, 204 and 208, are optionally molded into the first and second housing body halves or attached by means known to those skilled in the art. Alternatively, the third and fourth cantilever arms, 204 and 208, are optionally replaced with deformable devices at positions corresponding to the ramped protrusions, 205 and 207, and which are accepted in cavities defined by one or both of the first and second housing body halves.

E. Adaptation for a Single Occluding Device.

The drug delivery device of the present disclosure further includes embodiments of the first through fourth above described embodiments wherein one of the occluding devices is absent. In the absence of the occluding device at the proximate end of the respective drug cartridge, a closing device may be applied to the funnel bore to prevent the drug depot from falling out. In the absence of the occluding device at the distal end of the respective drug cartridge, a closing device may be applied to the nipple channel to prevent the drug depot from falling out.

F. Modification of Cantilever Arms.

The second, third and fourth embodiments of the present disclosure include the cantilever arms 194, 195, 204, and 208, respectively having ramped protrusions, 195, 197, 205, and 207. As shown in the figures, the protrusions, 195, 197, 205, and 207, are configured as bumps on the cantilever arms 194, 195, 204, and 208. It is considered to be within the scope and spirit of the present disclosure that in place of the ramped protrusions, 195, 197, 205, and 207, being distinct portions of the cantilever arms 194, 195, 204, and 208, the cantilever arms 194, 195, 204, and 208 may extend in a continuous manner angling into the depot channel so as to protrude sufficiently into the depot channel to prevent passage of a drug depot. As such, both the ramped protrusions, 195, 197, 205, and 207, and portions of the cantilever arms 194, 195, 204, and 208, modified to extend into the depot channel are considered to be "protruding portion(s)" of the cantilever arms 194, 195, 204, and 208.

Cannula

The cannula or needle of the drug delivery device is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The cannula or needle of the drug delivery device has an internal diameter that is larger than the diameter of at least part of the push rod 124 (e.g., tip, middle, etc.) of the plunger 120 to allow at least part of the plunger to be slidably received within the cannula or needle. In various embodiments, the diameter of the cannula or needle is substantially the same throughout. In other embodiments, the diameter of the needle or cannula becomes smaller approaching the distal end for drug delivery.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 17 to about 25 gauge.

In various embodiments and those described above, the plunger 120, cannula 110 or drug depot 140 include markings that indicate location at or near the site beneath the skin. Radiographic markers can be included on the drug depot to permit the user to accurately position the depot into the site of the patient. These radiographic markers will also permit the user to track movement and degradation of the depot at the site over time. In this embodiment, the user may accurately position the depot in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula 110 may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

Cannula Coupling Device

In various embodiments of the present disclosure, including those presented above, surrounding the opening of the proximal end of the cannula or needle is a generally cylindrical hub having an engagement means for engaging the housing body. In the above embodiments the housing bodies are shown having internal threading as part of a coupling device. This depiction of a portion of a coupling device is for exemplary purposes only and is not limiting. The present disclosure optionally includes alternative coupling devices which include, but are not limited to, threading, tracks, clips, ribs, projections, and the like that allow a secure connection between the housing and the proximal end of the cannula. For example, in various embodiments the coupling device may be a luer lock connection, where the cannula has mating threads that mate with the threads disposed on or in the housing.

Housing and Drug Cartridge Material

In various embodiments of the present disclosure, including those presented above, the housing is optionally formed of any of various shapes including, but not limited to, cylindrical or round such that the housing allows for the affixation to the cannula as well as acceptance of the drug cartridge and the plunger. In the embodiments presented above, the housings of the first through fourth embodiments include at least one side configured to prevent rolling of the housing. As illustrated, the housings optionally have a truncated circular cross section presenting opposing substantially flat sides which is an exemplary and non-limiting embodiment.

The housing is optionally provided with contours to allow easy grasping of the device during use for insertion of the drug depot. Furthermore, the housing is optionally angled for right and left hand users or can be generic for both hands.

The housing and drug cartridge is optionally comprised of any of a variety of materials, such as, for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof.

Informative Indicia

In various embodiments of the drug delivery device of the present disclosure, including those presented above, the housing is optionally provided with indicia such dose indicator markings (e.g., numbers, lines, letters, radiographic markers, etc.) to indicate a number and type of drug depots contained in the device and/or delivered into a patient. Additionally, expiration date, lot number, trademarks, application information, and classification of drug are optionally provided on the housing. The indicia is also optionally provided in the form of color coding of at least portions of the housing. Indicia in the third and fourth embodiments is optionally provided on the ring members thereof, but are also optionally provided elsewhere on the housing bodies. For exemplary purposes and without limitation, the ring members are color coded. In various embodiments, the plunger includes markings that indicate location at or near the site beneath the skin.

Plunger

In each of the aforesaid embodiments of the present disclosure the plunger knob 122 optionally has alignment ridges 125 which are configured to align the plunger knob 122 with any of the funnel bodies, 102, 102a-102c, by virtue of engagement with the funnel bore 150 when the plunger 120 is fully inserted into the drug delivery device. Additionally, the alignment ridges 125 provide structural support for the push rod 124.

Although the first end of the plunger is shown as a knob, it will be understood that the knob can be a top, dial, cap, handle or any member that allows the user to utilize the plunger. The plunger has a second end that includes a tip, which is capable of moving the drug depot within the cannula. In other embodiments, the tip of the plunger is sufficiently pointed so that it is capable of insertion to the site beneath the skin of the patient and the cannula or needle is blunted and used to guide the drug depot to the site.

The plunger has a diameter less than the cannula or needle so that it can be slidably received therein. The plunger may be longer, the same size, or smaller in length than the cannula or needle. In embodiments where the plunger extends from the distal end of the cannula or needle, the plunger is usually longer than the cannula or needle. In some embodiments, the tip of the plunger can be sharp or blunt.

The plunger may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The plunger may optionally include one or more tapered regions.

Like the cannula or needle, in various embodiments, the plunger may have dose indicator markings (e.g., numbers, lines, letters, radiographic markers, etc.) to indicate the number of drug depots delivered. In various embodiments, the plunger includes markings that indicate location at or near the site beneath the skin.

The plunger tip, which may be a complementary shape to the drug pellet, allows the plunger tip to snuggly fit within the end of the drug pellet for easier drug delivery. The drug pellet may have a rounded end for easier insertion at the desired site.

Drug Depot Composition and Manufacture

In various embodiments, including those described above, the drug delivery device optionally comprises at least one drug depot disposed therein during assembly. Alternatively, the drug delivery device is provided assembled without a drug therein and at least one drug depot is breach loaded in to the drug delivery device at a time of use. A further alternative is to provide the various components of the drug delivery device in a kit which allows loading of a drug depot into the drug cartridge of the respective device at the time of assembly.

A drug depot comprises a physical structure to facilitate implantation and retention in a desired site (e.g., a synovial joint, a disc space, a spinal canal, a tissue of the patient, etc.).

The drug depot also comprises the drug. The term "drug" as used herein is generally meant to refer to any substance that alters the physiology of the patient. The term "drug" may be used interchangeably herein with the terms "therapeutic agent", "therapeutically effective amount", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 mm to about 5 cm from the implant site.

Examples of drugs suitable for use in the drug depot, include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine[2-hydroxy-5-[-4-[C2-pyridinylamino) sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or protein inhibitors of TNF, such as etanercept, Remicade, IL-1, such as Kineret®, p38, RANK, RANKL, or a combination thereof.

Suitable osteoinductive factors include, but are not limited to, a bone morphogenetic protein, a growth differentiation factor, a LIM mineralization protein or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

A "depot" includes but is not limited to capsules, microspheres, particles, coating, matrices, wafers, pills, pellets or other pharmaceutical delivery compositions. In various embodiments, the depot may comprise a bioerodible, a bioabsorbable, and/or a biodegradable biopolymer that may provide immediate release, or sustained release of the drug. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide,-caprolactone, dextrans, vinylpyrrolidone, polyvinyl alcohol (PVA), PVA-g-PLGA, PEGT-PBT copolymer (poly-active), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. In various embodiments, the drug depot comprises poly(lactide-co-glycolide) (PLGA), polylactide (PLA), polyglycolide (PGA), D-lactide, D,L-lactide, L-lactide, D,L-lactide-$\epsilon$-caprolactone, D,L-lactide-glycolide-$\epsilon$-caprolactone or a combination thereof.

In various embodiments, the drug depot comprises drug pellets, as illustrated in the figures of the above described embodiments, loaded with a therapeutically effective amount of the therapeutic agent, wherein the pellets are injected into a synovial joint, a disc space, a spinal canal, or a soft tissue surrounding the spinal canal. In various embodiments, the drug pellets comprise a gel in viscous form and microspheres loaded with a therapeutic agent, wherein the combination of gel and microspheres are positioned into a synovial joint, disc space, a spinal canal, or a soft tissue surrounding the spinal canal of a subject.

A "therapeutically effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's pharmacokinetic properties, the route of administration, patient conditions and characteristics (sex, age, body weight, health, size, etc.), extent of symptoms, concurrent treatments, frequency of treatment and the effect desired.

In the above described exemplary embodiments, the drug depot is in the form of a pellet. The pellet can be any shape, such as for example, bullet shaped, spherical, substantially spherical, flaked, rod shaped (as presented in the figures), square, oval, etc. In various embodiments, the drug pellet has an aspect ratio (a ratio of the length of the pellet divided by the width found at an angle of 90° in respect to the length) which is less than about 1.4 to about 1.05.

The proximal end of the drug pellet may allow the plunger tip to snuggly fit within the proximal end of the drug pellet for easier drug delivery. The distal end of the drug pellet may be rounded for easier insertion at the site.

In various embodiments, the drug pellet comprises a bullet-shaped body that is made from a biodegradable material. In alternative embodiments, the body of the pellet may be made from a non-biodegradable material. A non-biodegradable body could be a porous hollow chamber filled with the therapeutic agent alone or incorporated into a degradable polymer. It may be desirable to make the body non-degradable to be able to retrieve it after it has released its contents. Non-limiting examples of suitable biodegradable materials for the pellet body include polyorthoesters (POE), polylacticglycolic acid (PLGA) polysacharides (Saber technology), polycapralactone, polyfumarate, tyrosine polycarbonate, etc. The body may be solid, and the therapeutic agent may be dispersed throughout the material that forms the body. The dispersal of the therapeutic agent may be even throughout the body. Alternatively, the concentration of the therapeutic agent may vary throughout the body. As the biodegradable material of the body degrades at the site, the therapeutic agent is released.

Procedures for making pellets include, but are not limited to, extrusion-spheroidization, for spherical pellets where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved, etc.) and the extrudate breaks into small cylinders, which in time are rounded into spherically shaped solids. Subsequently, the pellets are dried to the desired residual moisture content, typically in a fluid bed dryer. Any oversized or undersized product is removed by sieving, and the resulting pellets have a narrow size distribution.

In various embodiments, the API is layered on the solid core of the pellet by solution or suspension layering or powder layering techniques. In solution or suspension layering, an API and any inactive ingredients (excipients, binders, etc.) are suspended or dissolved in water or an organic solvent. The resulting liquid is sprayed onto the outside of a core particle, which may include, for example, non-pareil sugar seed (sugar sphere), microcrystalline cellulose pellets and the like, to make the pellet having the desired potency. Solution or suspension layering may be conducted using a wide variety of process techniques, for example, by fluidized bed, Wurster bottom spray techniques, or the like. When the desired potency has been achieved, pellets are dried to the desired residual moisture content. Any oversized or undersized product may be removed by sieving, and the resulting pellets are narrow in size distribution.

Powder layering may also be used to make the drug pellets. Powdered layering involves the application of a dry powder to the pellet core material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the core material while applying the dry powder until the desired potency is achieved. When the desired potency has been achieved, the pellets may be seal coated to improve their strength, and are then dried to the desired moisture content. Any oversized or undersized product is removed by sieving, and the resulting pellets are narrow in size distribution.

In one embodiment, the pellet is made using a core of biodegradable material, such as, for example, polyglactin, polylactone, polylactide, etc. The core is then coated with a thin layer of the API, such as an anti-inflammatory agent, analgesic agent, etc. by solution, suspension, or powdered layering until the desired potency is achieved.

In various embodiments, the drug pellets can be different sizes, for example, from about 1 mm to 5 mm in length and have a diameter of from about 0.01 to about 2 mm. The layer or layers will each have a layer thickness of from about 0.005 to 1.0 mm, such as, for example, from 0.05 to 0.75 mm.

Like the cannula, needle, or plunger, in various embodiments, the drug depot (e.g., pellet, cartridge, etc.) may have dose indicator markings (e.g., numbers, lines, letters, radiographic markers, etc.) to indicate the number of drug depots delivered. In various embodiments, radiopaque marks are positioned on the depot at opposite ends of the depot to assist in determining the position of the depot relative to the treatment site. For example, the radiopaque marker could be a spherical shape or a ring around the depot.

Drug Cartridge Material, Loading and Sterilization

In various embodiments, including those presented above, the drug cartridge may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or a combination thereof. In various embodiments, the drug cartridge is not biodegradable.

The drug device components (e.g., cannula or needle, plunger, housing, funnel body, etc.) are optionally lightweight, disposable and sterilizable such that when the device is assembled (e.g., the drug cartridge is loaded the housing), the weight of the device does not substantially increase. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, the drug cartridge provides the advantages of ease of manufacturing in the terminal sterilization process. If the drug pellets are preloaded in the manufacturing process, gamma radiation may be required at higher doses to sterilize the drug depot loaded in the cannula or needle. This is particularly so when the cannula or needle is made from steel or metal. Thus, to sterilize the loaded depot, the dose of gamma rays must be high enough to penetrate the metal, which may destroy the API in the drug depot. By providing a drug cartridge, for example, made of plastic, the drug cartridge and drug pellets in the cartridge can be sterilized, without destroying the API and then subsequently loaded by the manufacturer or the user (e.g., surgeon, physician, nurse, etc.). Further, loading the drug depot into the drug chamber or cannula is easier. This is particularly so when dealing with multi-dose drug pellets that are relatively small (e.g., 1 mm to 5 mm), the user typically cannot grasp these small pellets and load them into the device. By providing them in a drug cartridge, the user does not have to substantially manipulate the individual drug pellets and the risk of contaminating the pellets particularly with sterilized pellets is reduced.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot includes a gelatin capsule.

Other methods may also be used to sterilize one or more components of the device, including, but not limited to, gas sterilization, such as, for example, with ethylene oxide or steam sterilization.

In some embodiments, the housing, drug cartridge, and/or cannula are transparent so the user can see the position of the plunger and/or the drug depot in the chamber of the drug cartridge. Thus, indicator markings, in this embodiment, are not needed.

Drug Delivery Device Kit

In various embodiments, a kit is provided which may include additional parts along with the drug delivery device combined together to be used to implant the drug depot. The kit may include the drug delivery device in a first compartment. The second compartment may include the drug cartridge, and any other instruments needed for the implant. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

Method of Using the Drug Delivery Device

In various embodiments of the present disclosure, a method is provided for delivering a drug depot to a site beneath the skin of a patient, the method comprising: assembling a drug delivery device wherein the drug delivery device comprises a cannula having a proximal end and a distal end, the proximal end of the cannula having an opening to receive the drug depot, the distal end of the cannula capable of insertion to the site beneath the skin of the patient and having an opening for passage of the drug depot; a cartridge comprising components to form a secure chamber wherein the secure chamber is capable of storing one or more drug depots in the form of drug pellets, a housing having a top end, a bottom end, and an interior cavity wherein the bottom end of the housing has a coupling means for coupling to the proximal end of the cannula and wherein the interior cavity is configured to receive the cartridge; a plunger having a knob end and a tip end for expelling a drug pellet from the secure chamber, wherein the tip end is slidably receivable within each of the housing, the cartridge, and the cannula to deliver the drug pellet to the site beneath the skin of the patient; selecting a drug delivery site beneath the skin of the patient; and dispensing the drug pellet from the drug delivery device to a site beneath the skin of the patient.

In various embodiments, the seal between the plunger tip and the cannula or needle can be air tight so that when the cannula or plunger penetrates the skin, at times, fluid (e.g., blood, spinal fluid, synovial fluid, etc.) may be drawn up into the cannula or needle. This fluid will be expelled when the plunger is re-inserted into the cannula or needle and the drug depot is released.

The device may be used for localized and/or targeted delivery of the drug to a patient to treat a disease or condition such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, bone muscles, and the like.

In various embodiments, the drug delivery device is used to treat pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drugs depots in a quantity of pharmaceutical composition that can be deposited at the target site as needed for treatment of pain, inflammation or other disease or condition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A device for delivering a drug depot to a site beneath the skin of patient via a cannula having a proximal end and a distal end, the proximal end of the cannula having an opening to receive the drug depot, the distal end of the cannula being configured for insertion to the site beneath the skin of the patient and having an opening for passage of the drug depot, the device comprising:
    a housing having a top housing end, and a bottom housing end, said housing further defining a housing channel having a housing channel first open end open to said top housing end and a second housing channel open end open to said bottom housing end;
    a drug cartridge defining a depot channel aligned with said housing channel and configured to slidably accept the drug depot, said drug cartridge having a first and second occluding devices that are each configured to occlude said depot channel at an occluding position such that the drug depot cannot pass through said depot channel at said occluding positions without force, greater than that of gravity, applied to the drug depot sufficient to deflect one of said occluding devices an amount permitting passage of the drug depot past one of said occluding devices;
    said bottom housing end of said housing has a coupling configuration for engaging the proximal end of the cannula; and
    a plunger having a push rod slidably receivable in said housing channel and the cannula and having a push rod end to contact the drug depot when disposed in said drug cartridge and, upon application of force, expel the drug depot through said first occluding device and the cannula to the site beneath the skin of the patient,
    wherein said occluding position of said first occluding device is spaced apart from said occluding position of said second occluding device, said first and second occluding devices comprising first and second cantilever arms each having a protruding portion extending into said depot channel respectively at said first and second occluding positions.

2. A device for delivering a drug depot according to claim 1, wherein:
    said first occluding device is configured to occlude said drug depot channel at a first occluding position such that the drug depot cannot pass through said depot channel at said first occluding position without force, greater than that of gravity, applied to the drug depot sufficient to deflect said first occluding device an amount permitting passage of the drug depot past said first occluding device; and
    said second occluding device is configured to occlude said depot channel at a second occluding position, spaced apart from said first occluding position, such that the drug depot cannot pass through said depot channel at said second occluding positions without force, greater than that of gravity, applied to the drug depot sufficient to deflect said second occluding device an amount permitting passage of the drug depot past said second occluding device.

3. A device for delivering a drug depot according to claim 2, wherein said protruding portions extend into said depot channel respectively at said first and second occluding positions.

4. A device for delivering a drug depot according to claim 3, wherein said drug cartridge comprises:
    a first cartridge member having said first cantilever arm and a second cartridge member having said second cantilever arm; and
    a fastening structure connecting said first cartridge member and said second cartridge member together such that in conjunction with one another said first cartridge member and said second cartridge member define said depot channel.

5. A device for delivering a drug depot according to claim 4, wherein said housing channel has a funnel configuration extending from said housing channel first open end to a position proximate said depot channel so as to effect a tapering of width of said housing channel with approach to said depot channel.

6. A device for delivering a drug depot according to claim 5, wherein:
said housing has a viewing configuration disposed to permit viewing of a drug depot disposed in said drug cartridge; and
said drug cartridge is formed of a material permitting viewing of a drug depot held within said drug cartridge.

7. A device for delivering a drug depot according to claim 4, wherein:
said housing defines a receiving cavity for said drug cartridge; and
said drug cartridge comprises said first and second cartridge members having a configuration, when fastened together by said fastening structure, permitting insertion of said drug cartridge into said receiving cavity.

8. A device for delivering a drug depot according to claim 1, wherein said drug cartridge comprises a funnel body having a tapered passageway that is aligned with said depot channel.

9. A device for delivering a drug depot according to claim 1, wherein said drug cartridge comprises a first cartridge plate and a second cartridge plate.

10. A device for delivering a drug depot according to claim 9, wherein said second cartridge plate is integrally formed with a funnel body having a tapered passageway that is aligned with said depot channel.

11. A device for delivering a drug depot according to claim 9, wherein said first cartridge plate snaps onto said second cartridge plate by means of cantilever catch hook arms engaging a distal end of said first cartridge plate 200.

12. A device for delivering a drug depot according to claim 11, wherein a proximate end of said first cartridge plate is engaged with hinging apertures of a funnel body having a tapered passageway that is aligned with said depot channel.

13. A device for delivering a drug depot according to claim 12, wherein said second cartridge plate is integrally formed with said funnel body.

14. A device for delivering a drug depot according to claim 1, wherein said protruding portions each include a ramped protrusion.

15. A device for delivering a drug depot according to claim 1, wherein said housing comprises an internal thread and said device further comprises a cannula having an external thread that engages said internal thread.

16. A device for delivering a drug depot according to claim 1, further comprising said drug depot, wherein said drug depot is positioned within said depot channel.

17. A device for delivering a drug depot according to claim 16, wherein said drug depot comprises clonidine.

18. A kit for delivering a drug depot to a site beneath the skin of a patient in conjunction with a cannula having a proximal end and a distal end, the proximal end of the cannula having an opening to receive the drug depot, the distal end of the cannula being configured for insertion to the site beneath the skin of the patient and having an opening for passage of the drug depot, the kit comprising:
a housing having a top housing end, and a bottom housing end, said housing further defining a housing channel having a housing channel first open end open to said top housing end and a second housing channel open end open to said bottom housing end;
a drug cartridge defining a depot channel disposed to be aligned with said housing channel and configured to slidably accept the drug depot, said drug cartridge having first and second occluding devices that are each configured to occlude said depot channel at an occluding position such that the drug depot cannot pass through said depot channel at said occluding positions without force, greater than that of gravity, applied to the drug depot sufficient to deflect one of said occluding devices an amount permitting passage of the drug depot past one of said occluding devices;
said bottom housing end of said housing having a coupling configuration for engaging the proximal end of the cannula; and
a plunger having a push rod slidably receivable in said housing channel and the cannula and having a push rod end to contact the drug depot when disposed in said drug cartridge and, upon application of force, expel the drug depot through either of the first occluding device and the cannula to the site beneath the skin of the patient,
wherein said first and second occluding devices are first and second cantilever arms each having a protruding portion extending into said depot channel respectively at said first and second occluding positions.

19. A kit for delivering a drug depot according to claim 18, wherein:
said housing defines a cartridge cavity configured to accept said drug cartridge; and
said drug cartridge comprises:
a first cartridge member having said first cantilever arm and a second cartridge member having said second cantilever arm; and
a fastening structure connecting said first cartridge member and said second cartridge member together such that, in conjunction with one another, said first cartridge member and said second cartridge member define said depot channel and, when assembled together, are insertable into said cartridge cavity.

20. A device for delivering a drug depot to a site beneath the skin of patient via a cannula having a proximal end and a distal end, the proximal end of the cannula having an opening to receive the drug depot, the distal end of the cannula being configured for insertion to the site beneath the skin of the patient and having an opening for passage of the drug depot, the device comprising:
a housing having a top housing end, and a bottom housing end, said housing further defining a housing channel having a housing channel first open end open to said top housing end and a second housing channel open end open to said bottom housing end;
a drug cartridge defining a depot channel aligned with said housing channel and configured to slidably accept the drug depot, said drug cartridge having at least a first occluding device configured to occlude said depot channel at a first occluding position such that the drug depot cannot pass through said depot channel at said first occluding position without force, greater than that of gravity, applied to the drug depot sufficient to deflect said first occluding device an amount permitting passage of the drug depot past said first occluding device;
said bottom housing end of said housing has a coupling configuration for engaging the proximal end of the cannula; and
a plunger having a push rod slidably receivable in said housing channel and the cannula and having a push rod end to contact the drug depot when disposed in said drug cartridge and, upon application of force, expel the drug depot through said first occluding device and the cannula to the site beneath the skin of the patient,
wherein said drug cartridge includes a second occluding device configured to occlude said depot channel at a second occluding position, spaced apart from said first occluding position, such that the drug depot cannot pass through said depot channel at said second occluding positions without force, greater than that of gravity, applied to the drug depot sufficient to deflect said second occluding device an amount permitting passage of the drug depot past said second occluding device, and wherein said first and second occluding devices are first and second cantilever arms each having a protruding portion extending into said depot channel respectively at said first and second occluding positions.

* * * * *